United States Patent
Matsuzaki et al.

(10) Patent No.: US 11,724,017 B2
(45) Date of Patent: Aug. 15, 2023

(54) DIALYSIS APPARATUS AND PRIMING METHOD FOR DIALYSIS APPARATUS

(71) Applicant: SHIBUYA CORPORATION, Kanazawa (JP)

(72) Inventors: Kosho Matsuzaki, Kanazawa (JP); Takashi Mishima, Kanazawa (JP)

(73) Assignee: SHIBUYA CORPORATION, Kanazawa (JP)

( * ) Notice: Subject to any disclaimer, the term of this patent is extended or adjusted under 35 U.S.C. 154(b) by 158 days.

(21) Appl. No.: 17/520,840

(22) Filed: Nov. 8, 2021

(65) Prior Publication Data

US 2022/0143288 A1 May 12, 2022

(30) Foreign Application Priority Data

Nov. 12, 2020 (JP) ................................ 2020-188817

(51) Int. Cl.
*A61M 1/36* (2006.01)

(52) U.S. Cl.
CPC ........ *A61M 1/3649* (2014.02); *A61M 1/3647* (2014.02); *A61M 1/3656* (2014.02); *A61M 2205/3337* (2013.01)

(58) Field of Classification Search
None
See application file for complete search history.

(56) References Cited

U.S. PATENT DOCUMENTS

| 9,205,247 | B2 | 12/2015 | Ueda et al. |
| 9,592,330 | B2 | 3/2017 | Mishima et al. |
| 9,872,951 | B2 | 1/2018 | Furuhashi et al. |
| 2019/0201604 | A1* | 7/2019 | Hogard ............... A61M 1/3643 |

FOREIGN PATENT DOCUMENTS

| EP | 2397695 A1 * | 12/2011 | .......... F04B 43/0072 |
| JP | 5397747 B2 | 9/2010 | |
| JP | 5920575 B2 | 12/2013 | |
| JP | 5999333 B2 | 2/2014 | |
| JP | 6685374 B2 | 4/2019 | |

* cited by examiner

Primary Examiner — Jonathan M Peo
(74) Attorney, Agent, or Firm — Flynn Thiel, P.C.

(57) ABSTRACT

A dialysis apparatus has a connection channel that communicatively connects a dialysate circuit and a blood circuit, and circulates dialysate from the dialysate circuit to the blood circuit via the connection channel during a priming operation. A blood pump has a tube attachment device that switches from an unattached state in which a tube is positioned outside a housing and permits liquid to circulate thereinside, to an attached state in which the tube is in the housing and a rotor compresses the tube. At the time of priming, the liquid feeding pump feeds dialysate from the dialysate circuit to the blood circuit via the connection channel. With the blood pump being in the unattached state, the dialysate is circulated past the blood pump, and then, with the blood pump in the attached state, the dialysate is circulated in a direction opposite to the blood pump.

7 Claims, 18 Drawing Sheets

[STEP 1]

[STEP 2]

[STEP 3]

[STEP 4]

[STEP 1]

[STEP 2]

[STEP 3]

[STEP 4]

[STEP 5]

[STEP 1]

[STEP 2]

[STEP 3]

[STEP 4]

DIALYSIS APPARATUS AND PRIMING METHOD FOR DIALYSIS APPARATUS

BACKGROUND OF THE INVENTION

Field of the Invention

The present invention relates to a dialysis apparatus and a priming method for a dialysis apparatus, more specifically to a dialysis apparatus provided with a blood circuit and a dialysate circuit, and a priming method for a dialysis apparatus that circulates a dialysate from the dialysate circuit to the blood circuit to fill the blood circuit with the dialysate.

Description of the Related Art

A dialysis apparatus used in hemodialysis and the like has a configuration in which a blood circuit that circulates blood and a dialysate circuit that circulates a dialysate are connected to a dialyzer that carries out hemodialysis.

In such a dialysis apparatus, a new dialyzer and a new blood circuit are attached to the dialysis apparatus for each course of dialysis treatment, leading to the necessity of priming, during which the dialyzer and the blood circuit are filled with a priming liquid.

As a method for carrying out the priming, a method of circulating a dialysate from the dialysate circuit to the blood circuit to fill the blood circuit with the dialysate has been known, in which a blood pump provided in the blood circuit is used for circulating the dialysate in the entire blood circuit during the priming operation (Japanese Patent No. 6685374).

As the blood pump, a so-called tube pump has been typically used; however, such a tube pump is poor in liquid feeding performance, leading to a problem of making circulation of the dialysate in the entire blood circuit time-consuming.

In addition, in order that air bubbles would not flow into the patient's body during the treatment, every air bubble in the blood circuit needs to be removed during the priming operation; however, the tube pump poor in liquid feeding performance leads to a problem of not being capable of efficiently removing air bubbles remaining in the blood circuit.

In view of the above-described problems, the present invention is directed to providing a dialysis apparatus and a priming method that enable a reduction in time required for the priming operation and efficient removal of air bubbles remaining in the blood circuit.

SUMMARY OF THE INVENTION

A dialysis apparatus according to an invention of claim 1 includes: a dialyzer in which a blood chamber and a dialysate chamber are formed; a blood circuit that circulates blood to the blood chamber in the dialyzer; a dialysate circuit that circulates dialysate to the dialysate chamber in the dialyzer; a liquid feeding pump that is provided in the dialysate circuit and feeds the dialysate; a connection channel that communicatively connects the dialysate circuit and the blood circuit; and a blood pump provided with a housing that houses an elastic tube comprised in the blood circuit and a rotor that rotates inside the housing to rotate the tube while compressing the tube, the dialysate being circulated from the dialysate circuit to the blood circuit via the connection channel during a priming operation, and is characterized in that:

the blood pump comprises a tube attachment device that switches from an unattached state in which the tube is positioned outside the housing and permits a liquid to circulate thereinside, to an attached state in which the tube is housed in the housing and the rotor compresses the tube to block the tube; and during the priming operation, with the blood pump being in the unattached state, the liquid feeding pump feeds the dialysate from the dialysate circuit to the blood circuit via the connection channel and, when a predetermined amount of the dialysate has circulated past the blood pump, the tube attachment device puts the blood pump into the attached state.

A priming method for a dialysis apparatus according to an invention of claim 5, the dialysis apparatus including: a dialyzer in which a blood chamber and a dialysate chamber are formed; a blood circuit that circulates blood to the blood chamber in the dialyzer; a dialysate circuit that circulates dialysate to the dialysate chamber in the dialyzer; a liquid feeding pump that is provided in the dialysate circuit and feeds the dialysate; a connection channel that communicatively connects the dialysate circuit and the blood circuit; and a blood pump provided with a housing that houses an elastic tube comprised in the blood circuit and a rotor that rotates inside the housing to rotate the tube while compressing the tube, the dialysate being circulated from the dialysate circuit to the blood circuit via the connection channel during a priming operation, is characterized in that, during the priming operation, the tube is detached from the housing to be in an unattached state in which a liquid is permitted to circulate thereinside, and then the liquid feeding pump feeds the dialysate from the dialysate circuit to the blood circuit via the connection channel to circulate the dialysate to a portion past the blood pump.

According to the above-described invention, due to feeding the dialysate from the dialysate circuit to the blood circuit by means of the liquid feeding pump provided in the dialysate circuit, the amount of liquid being fed can be increased compared to the case of feeding the dialysate by means of the blood pump, whereby the dialysate can be quickly circulated in the blood circuit, enabling efficient removal of air bubbles.

In addition, although the blood pump is not used for feeding liquid, by switching the blood pump from the unattached state to the attached state, that is from a state in which circulation of the dialysate is permitted in a tube to a state in which the circulation of the dialysate is blocked by the rotor compressing the tube, the circulation direction of the dialysate in the blood circuit can be controlled to thereby fill the entire blood circuit with the dialysate.

BRIEF DESCRIPTION OF THE DRAWINGS

FIG. 2 is a circuit diagram of the dialysis apparatus according to the first embodiment;

DETAILED DESCRIPTION OF THE PREFERRED EMBODIMENTS

Figure 1:
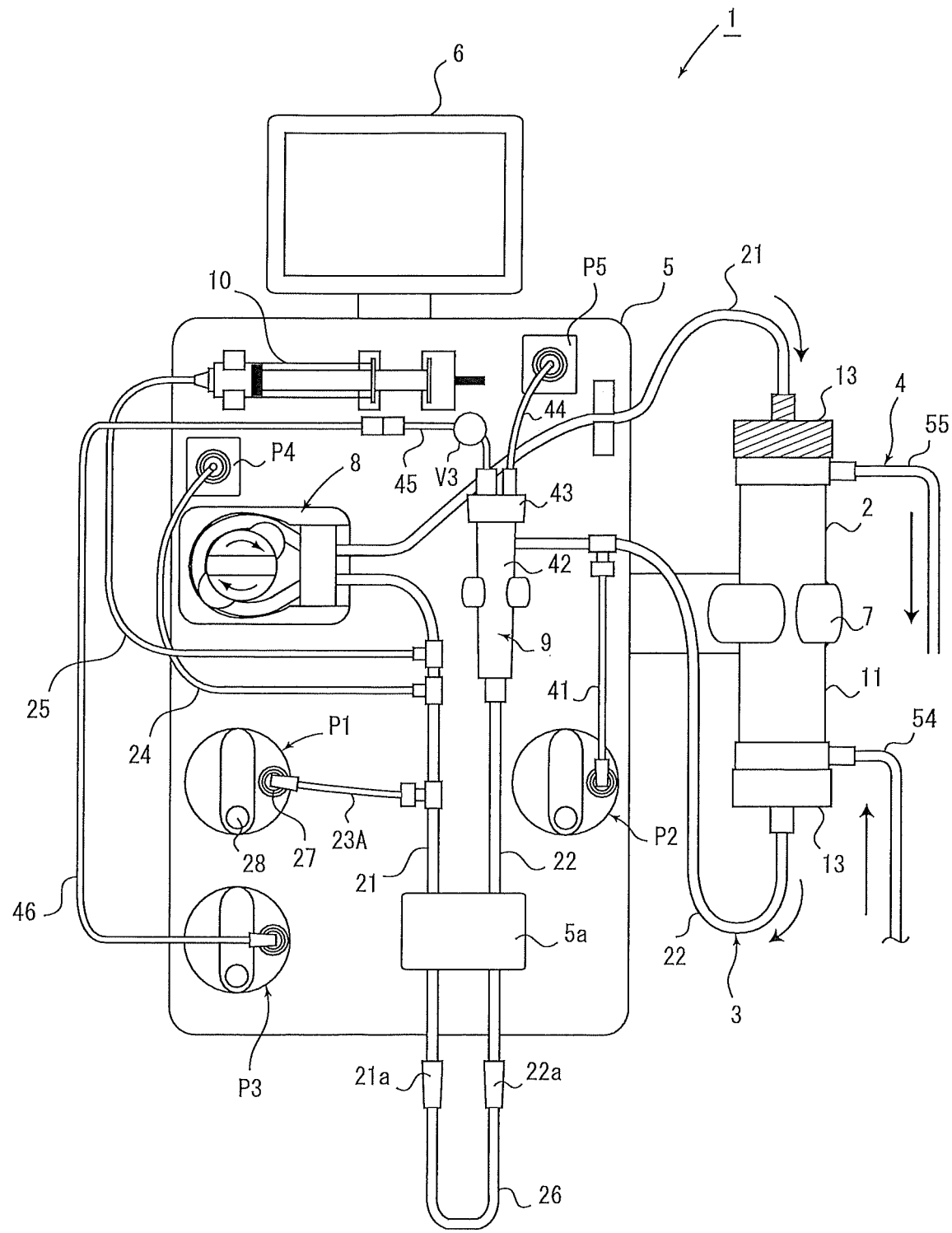
FIG. 1 is a front view of a dialysis apparatus according to a first embodiment.
Figure 2:
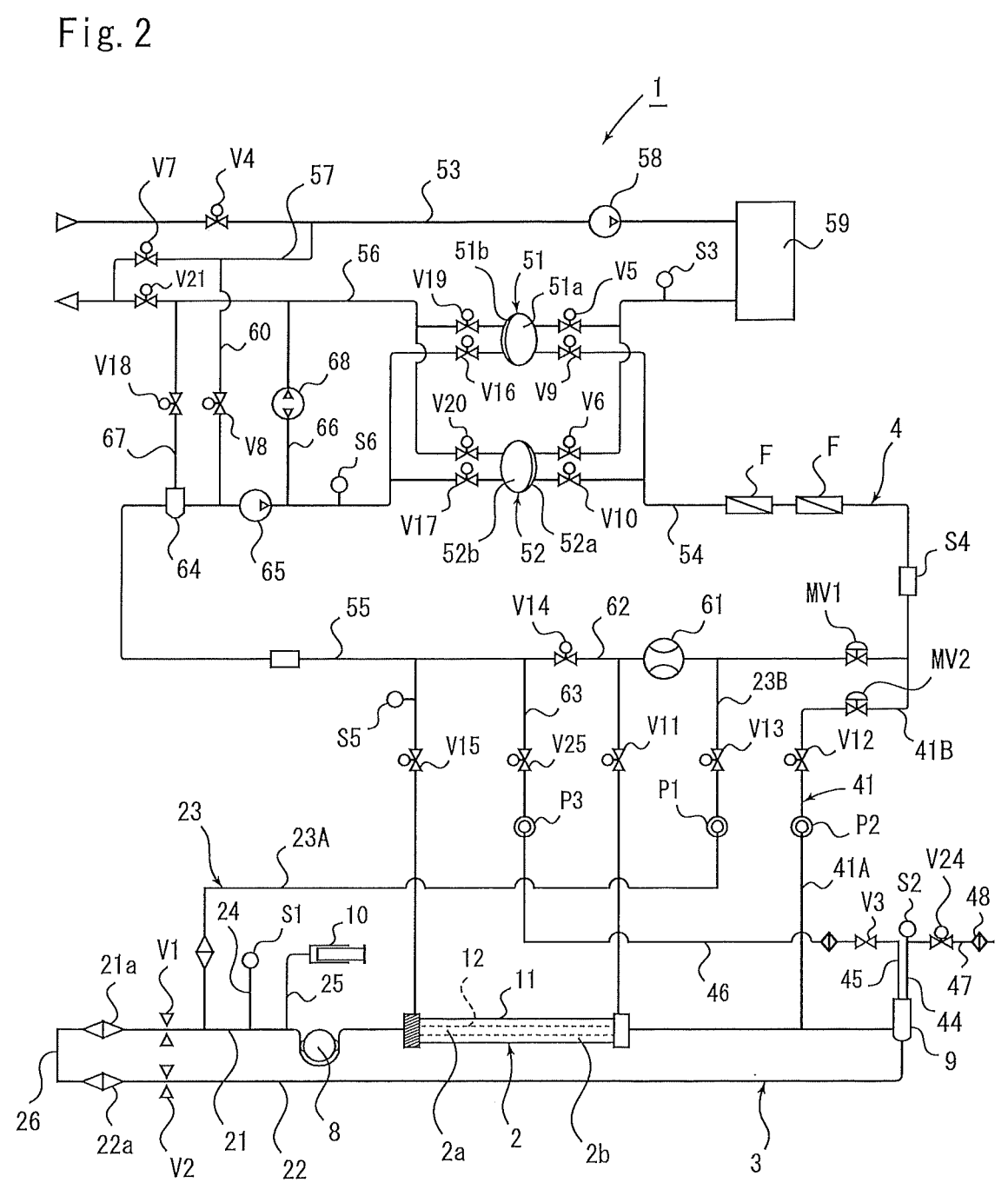

The embodiments illustrated in the drawings are described hereinafter. FIG. 1 shows a front view of a dialysis apparatus 1 according to the present embodiment, and FIG. 2 shows a circuit diagram of the dialysis apparatus 1.

The dialysis apparatus 1 is configured to be controlled by a control device not illustrated, and is provided with: a dialyzer 2 carrying out hemodialysis; a blood circuit 3 that circulates blood to the dialyzer 2; and a dialysate circuit 4 that circulates a dialysate to the dialyzer 2.

As shown in FIG. 1, the most part of the blood circuit 3 is configured to be exposed to a front face of a main body portion 5 comprised in the dialysis apparatus 1, while the most part of the dialysate circuit 4 is housed inside the dialysis apparatus 1.

In addition, on an upper portion of the main body portion 5, a touch panel 6 for displaying a status and the like of a patient and for performing necessary operations is provided, and on a lateral face, a dialyzer holder 7 for holding the dialyzer 2 is provided.

Furthermore, on a front face of the main body portion 5, a blood pump 8 comprised in the blood circuit 3, a drip chamber 9, and a syringe 10 for infusion of a pharmaceutical preparation are held, and first to third connection ports P1 to P3 provided at an end portion of the dialysate circuit 4, and first and second sensor ports P4, P5 for connecting the blood circuit 3 to a sensor for the blood circuit 3 provided in the main body portion 5 are provided.

FIG. 1 and FIG. 2 show a state during the priming operation of the dialysis apparatus 1. As used herein, the "priming operation" means an operation of connecting the dialyzer 2 and the blood circuit 3 to the dialysis apparatus 1 and filling the dialyzer 2 and the blood circuit 3 with the dialysate prior to the dialysis treatment.

Note that, in the following description of the dialysis apparatus 1, configurations related to the priming operation are described, while illustration and description of configurations not directly related thereto are omitted.

The dialyzer 2 is provided with a tubular portion 11 made of a resin, and a plurality of hollow fibers 12 provided inside the tubular portion 11, with an inner portion of the hollow fibers 12 forming a blood chamber 2a, and an outer portion of the hollow fibers 12 forming a dialysate chamber 2b in which the dialysate circulates.

A cap 13 is provided in both end portions of the tubular portion 11, with the blood circuit 3 being connected to the center of the cap 13 and communicatively connected to the blood chamber 2a, and the dialysate circuit 4 being connected to a lateral portion of the cap 13 and communicatively connected to the dialysate chamber 2b.

In addition, as shown in FIG. 1, the dialyzer 2 is held by the dialyzer holder 7 such that the caps 13 are positioned up and down, and at the time of the dialysis treatment, blood circulates from an upper side to a lower side of the blood chamber 2a in the drawings (from a left side to a right side in FIG. 2), while the dialysate circulates from a lower side to an upper side of the dialysate chamber 2b in the drawings (from a right side to a left side in FIG. 2).

The blood circuit 3 is provided with: an artery-side channel 21 for feeding blood from the artery of the patient to the blood chamber 2a of the dialyzer 2, and a vein-side channel 22 for returning blood from the blood chamber 2a to the vein of the patient, the artery-side channel 21 being connected to an upper portion of the dialyzer 2 and the vein-side channel 22 being connected to a lower portion of the dialyzer 2 in FIG. 1.

In FIG. 2, a connector 21a, to which a puncture needle is to be attached at the time of treatment, is provided in an end portion of the artery-side channel 21. From a position adjacent to the connector 21a: an artery-side clamp V1 controlled by the control device; a retransfusion channel 23A as the connection channel used for returning blood in the blood circuit 3 to the patient after the dialysis treatment; a pressure measurement channel 24 connected to an artery-side pressure sensor S1 provided in the main body portion 5; and a pharmaceutical preparation supply channel 25 connected to the syringe 10, are provided in this order.

Furthermore, the blood pump 8 is provided between the pharmaceutical preparation supply channel 25 and the dialyzer 2 on the artery-side channel 21.

The puncture needle is to be attached to the connector 21a of the artery-side channel 21 and to be inserted into the artery of the patient at the time of the dialysis treatment. On the other hand, during the priming as shown in FIG. 1 and FIG. 2, one end of a first priming piping 26 is to be connected to the connector 21a.

The artery-side clamp V1 is housed in a case 5a provided on a front face of the main body portion 5, and the connector 21a of the artery-side channel 21 is positioned on a lower side of the case 5a in the drawing.

The retransfusion channel 23A configures a part of the connection channel of the present invention, and is connected to the first connection port P1 provided in an end portion of a retransfusion channel 23B comprised in the dialysate circuit 4 as described later, to configure the retransfusion channel 23.

The first connection port P1 is provided on the front face of the main body portion 5, and the second and third connection ports P2, P3 described later have the same configuration as the first connection port P1. As such a connection port P, the configuration disclosed in Japanese Patent No. 5920575 may be employed.

The configuration is conventionally well-known and therefore detailed description is omitted herein. The first connection port P1 comprises: a connector 27 provided in the end portion of the retransfusion channel 23B comprised in the dialysate circuit 4; and a lid member 28 rotatably provided on the front face of the main body portion 5.

The connector 27 is provided to be exposed on the surface of the main body portion 5, and may be exposed to the outside and covered not to be exposed to the outside, through rotation of the lid member 28.

On the other hand, a connector is provided also in the end portion of the retransfusion channel 23A on the blood circuit 3 side, and, at the time of the dialysis treatment, the retransfusion channel 23A and the retransfusion channel 23B are to be communicatively connected through rotating the lid member 28 of the first connection port P1 to expose the connector 27 of the retransfusion channel 23B and connecting the connector of the retransfusion channel 23A thereto.

In FIG. 1, the artery-side pressure sensor S1 is provided with a first sensor port P4 on the front face of the main body portion 5, and an end portion of the pressure measurement channel 24 is to be connected to the first sensor port P4.

The syringe 10 containing a pharmaceutical preparation is connected to an end portion of the pharmaceutical preparation supply channel 25 and held on the front face of the main body portion 5 as shown in FIG. 1, and the pharmaceutical preparation is to be supplied from the syringe 10 to the blood circuit 3 at the time of the dialysis treatment.

Figure 3:
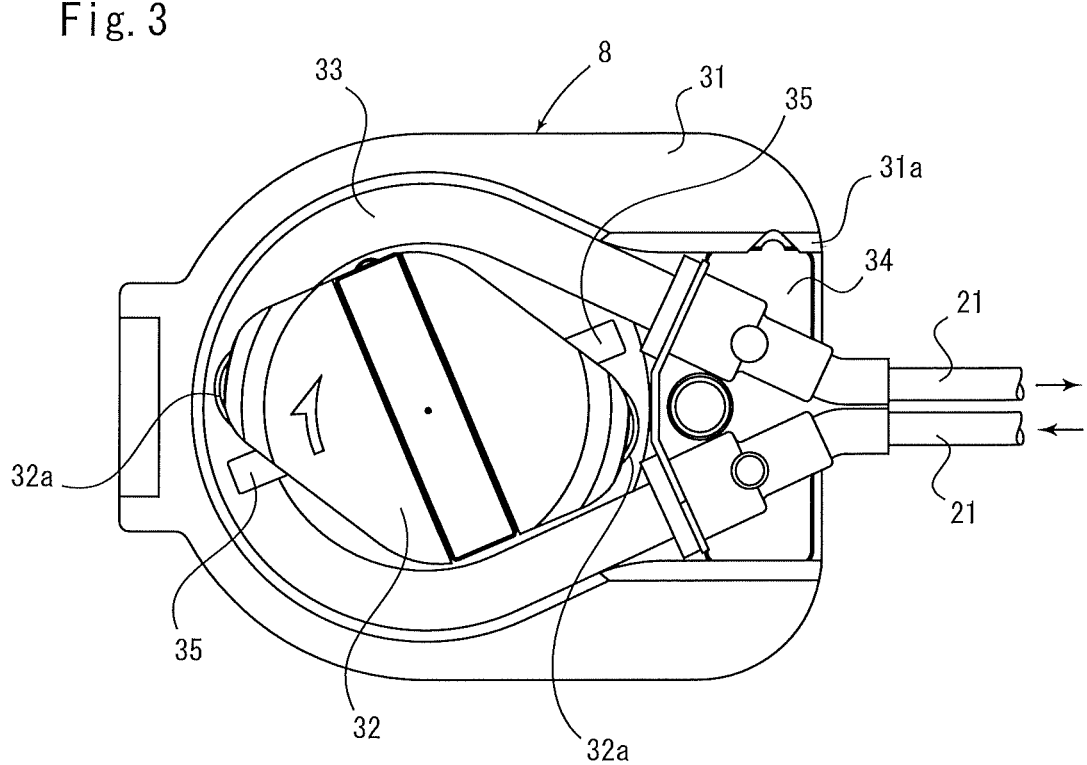
FIG. 3 is a plan view of a blood pump.
Figure 4:
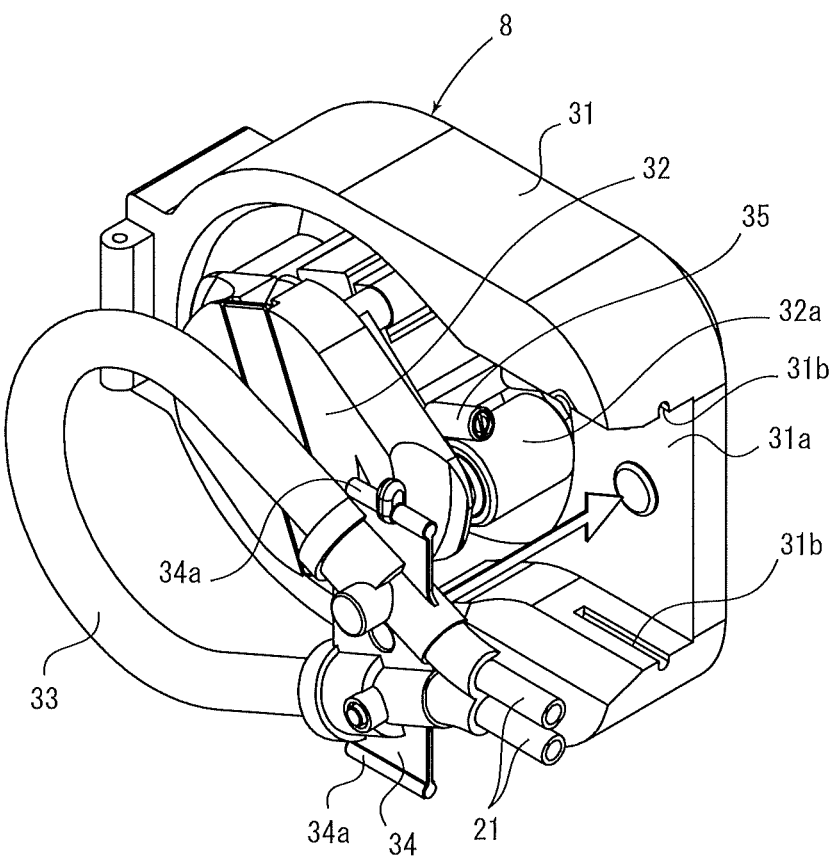
FIG. 4 is a perspective view of a blood pump.
Figure 5:
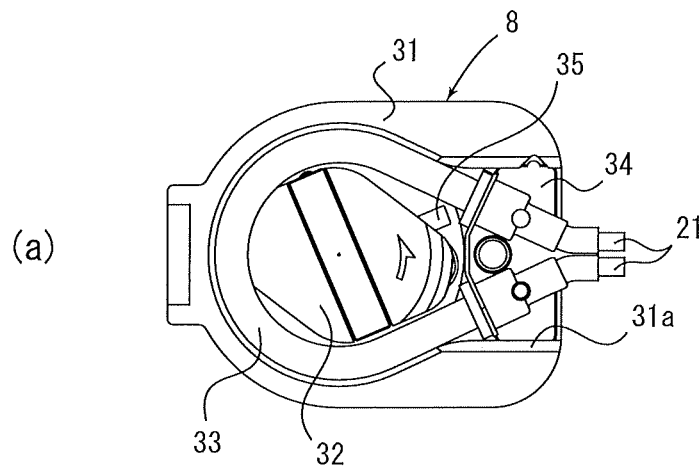
FIG. 5 is a diagram illustrating an operation of the blood pump.
Figure 5:
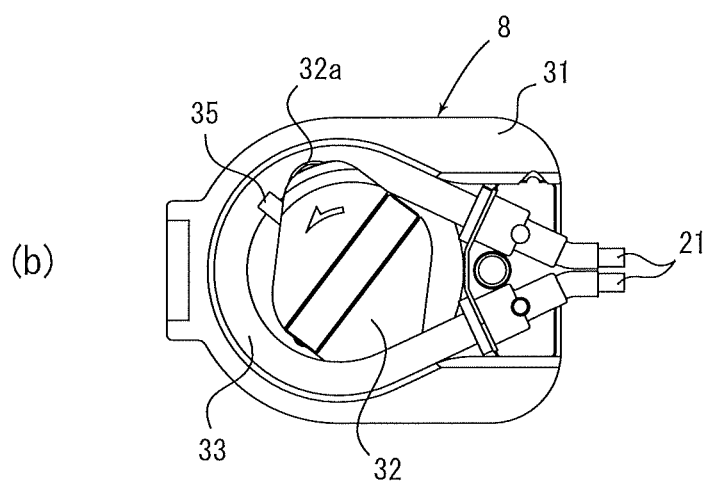
Figure 5:
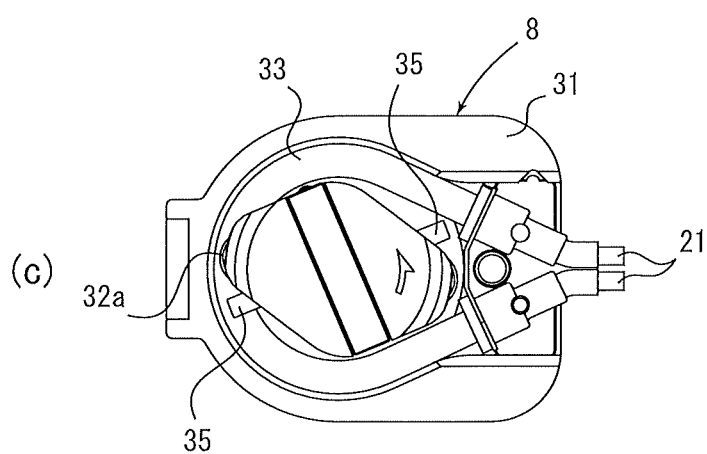

As the blood pump 8, the configuration as shown in FIGS. 3 to 5, disclosed in Japanese Patent No. 5397747, for example, may be employed. FIG. 3 shows a front view of the blood pump 8, FIG. 4 shows a perspective view of the blood pump 8, and FIG. 5 shows an operating state of the blood pump 8.

The blood pump 8 is conventionally well-known and therefore detailed description thereof is omitted herein. The blood pump 8 is a so-called tube pump provided with a housing 31 arranged in a perpendicular direction on the front face of the main body portion and a rotor 32 rotated inside the main body portion 5.

The blood pump 8 is to be used in a state in which a tube 33 configuring the artery-side channel 21 is deformed in a horseshoe shape (substantially U-shape) and accommodated between the housing 31 and the rotor 32.

A roller 32a is provided in an outer periphery of the rotor 32 to compress the tube 33 between the roller 32a and an inner wall of the housing 31. As the rotor 32 is rotated, the roller 32a moves while compressing the tube 33 to push to feed the liquid inside the tube 33.

The blood pump 8 of the present embodiment is further provided with a tube attachment device that automatically presses the tube 33 into a gap between the housing 31 and the rotor 32.

At this moment, the tube 33 being used has a greater diameter than other portion configuring the artery-side channel 21, and in a state of being deformed in a horseshoe shape, both end portions thereof are each held by a holder 34 made of a resin.

To the both end portions of the tube 33 each held by the holder 34, other portions of the artery-side channel 21 are respectively connected. A holding portion 31a for holding the holder 34 is provided in a position adjacent to a portion housing the rotor 32 and the tube 33 in the housing 31.

More specifically, bar-like protrusions 34a are respectively formed in an upper portion and a lower portion of the holder 34, and engagement grooves 31b with which the bar-like protrusions 34a engage are formed on the holding portion 31a.

Such a configuration enables a healthcare worker to attach the blood circuit 3 to the blood pump 8 by engaging the bar-like protrusions 34a on the holder 34 with the engagement grooves 31b formed on the holding portion 31a of the housing 31.

At this moment, the healthcare worker does not need to press the tube 33 into the gap between the housing 31 and the rotor 32, because the tube attachment device automatically attach the tube 33 during the priming operation described later.

The tube attachment device comprises a guide pin 35 provided in a position adjacent to the roller 32a of the rotor 32, the guide pin 35 being configured to press the tube 33 into the gap between the housing 31 and the rotor 32 as the rotor 32 rotates.

Hereinafter, the operation of the tube attachment device is described with reference to FIG. 5. FIG. 5(a) shows an unattached state in which the holder 34 has attached the tube 33 to the blood pump 8, but the tube 33 is not housed in the housing 31.

In this unattached state, the tube 33 is positioned in front of the housing 31 and the rotor 32 and is therefore not compressed by the housing 31 and the rotor 32, thus permitting a liquid to circulate inside the tube 33.

When the rotor 32 is rotated from the unattached state of the tube 33, the guide pin 35 engages with the portion of the tube 33 adjacent to the holder 34 as shown in (b), and when the rotor 32 is further rotated, the guide pin 35 presses the tube 33 into the gap between the housing 31 and the rotor 32.

And then, when the rotor 32 is further rotated, as shown in (c), the entire tube 33 is pressed into the gap between the housing 31 and the rotor 32, whereby the attached state is obtained in which the tube 33 is housed in the housing 31.

In this attached state, the tube 33 is housed between the housing 31 and the rotor 32, and is partially compressed by the rotor 32, preventing a liquid from circulating inside the tube 33.

As described above, by putting the blood pump 8 into the unattached state shown in (a), a liquid is permitted to circulate inside the tube 33, and to circulate past the blood pump 8.

On the other hand, by putting the blood pump 8 into the attached state shown in (c), a liquid is blocked from circulating inside the tube 33, and prevented from circulating past the blood pump 8.

In other words, by switching the blood pump 8 from the unattached state to the attached state, the blood pump 8 can be used like a valve.

Note that the blood pump 8 is not limited to the above-described configuration, and may be a pump in which the rotor 32 is provided with three or more rollers 32a, or a pump in which the tube 33 is housed in the housing 31 in a state in which a corner portion is bent at substantially 90°, not in a state of being substantially horseshoe-shaped.

Next, the vein-side channel 22 is connected to the lower end portion of the dialyzer 2 in FIG. 1, and provided with a connector 22a, to which the puncture needle is to be attached at the time of the dialysis treatment, in an end portion.

As shown in FIG. 2, the vein-side channel 22 is further provided with: an infusion channel 41A for use in infusion during the dialysis treatment; the drip chamber 9 that removes air from the circulating blood; and a vein-side clamp V2 controlled by the control device, in this order from the dialyzer 2 side.

The connector 22a of the vein-side channel 22 is positioned on the lower side with respect to the case 5a of the main body portion 5 in FIG. 1, and during the priming, the first priming piping 26 is connected to the connector 22a to be communicatively connected to the artery-side channel 21.

Furthermore, the vein-side clamp V2 is housed in the case 5a in FIG. 1. In this embodiment, the artery-side clamp V1 of the artery-side channel 21 and the vein-side clamp V2 are housed in the same case 5a.

A connector is provided in an end portion of the infusion channel 41A, and, at the time of the dialysis treatment, connected to the second connection port P2 provided at an end portion of an infusion channel 41B comprised in the dialysate circuit 4, to configure the infusion channel 41 as the connection channel according to the present invention.

The drip chamber 9 comprises: a tubular container 42 held on the front face of the main body portion 5 of the dialysis apparatus 1; and a cap 43 attached to an upper portion of the container 42, as shown in FIG. 1. A channel on the dialyzer 2 side of the vein-side channel 22 is connected to an upper lateral face of the container 42, and a channel on the connector 22a side is connected to a lower end portion of the container 42.

To the cap 43 of the drip chamber 9, a vein-side pressure sensor S2 is connected via a pressure measurement channel 44, and an overflow channel 45 for discharging a liquid in the container 42 is connected.

The vein-side pressure sensor S2 is provided with a second sensor port P5 on the front face of the main body portion 5, and the pressure measurement channel 44 is to be connected to the second sensor port P5 at the time of the dialysis treatment.

In addition, a liquid level adjustment channel 47 is connected to the pressure measurement channel 44, the liquid level adjustment channel 47 being provided with: a twenty-fourth valve V24 controlled by the control device; and an air filter 48. Consequently, it is made possible for a healthcare worker to appropriately adjust the liquid level in the container 42 by operating on the touch panel 6 to activate the twenty-fourth valve V24.

At the time of the priming operation, a second priming piping 46 is connected to an end portion of the overflow channel 45, the second priming piping 46 being connected to the third connection port P3 of a priming channel 63, described later, configuring the dialysate circuit 4.

After the completion of the priming operation, the second priming piping 46 is removed from the overflow channel 45 and the third connection port P3.

The overflow channel 45 is provided with a manually-operated clamp V3. Upon removal of the second priming piping 46, a healthcare worker operates the clamp V3 to shut-off the overflow channel 45 in advance.

Next, the dialysate circuit 4 is described. The dialysate circuit 4 is provided with: first and second dialysate chambers 51, 52 in which supply chambers 51a, 52a and collection chambers 51b, 52b are respectively formed by a diaphragm; a liquid replenishment channel 53 that supplies purified water to the supply chambers 51a, 52a; a dialysate supply channel 54 that supplies the dialysate from the supply chambers 51a, 52a to the dialyzer 2; a dialysate collection channel 55 that collects the used dialysate from the dialyzer 2 to the collection chambers 51b, 52b; and a discharge channel 56 that discharges the used dialysate from the collection chambers 51b, 52b.

The purified water and a stock solution of the dialysate alternately flow from the liquid replenishment channel 53 into the supply chambers 51a, 52a in the first and second dialysate chambers 51, 52, whereby the dialysate is prepared inside the supply chambers 51a, 52a.

As the purified water and the stock solution flow into the supply chambers 51a, 52a, the diaphragm deforms to discharge the used dialysate, by an amount equivalent to the inflow amount, from the collection chambers 51b, 52b to the discharge channel 56.

On the other hand, the used dialysate having passed through the dialyzer 2 flows from the dialysate collection channel 55 alternately into the collection chambers 51b, 52b, whereby the diaphragm deforms to supply new dialysate, by an amount equivalent to the inflow amount, from the supply chambers 51a, 52a into the dialyzer 2 via the dialysate supply channel 54.

An upstream-side end portion of the liquid replenishment channel 53 is connected to a water supply source, not illustrated, that supplies the purified water. The liquid replenishment channel 53 is provided with: a fourth valve V4 controlled by the control device; a first bypass channel 57 communicatively connected to the discharge channel 56; a liquid replenishment pump 58 as the liquid feeding pump that feeds the purified water; a dialysate stock solution supply device 59 that supplies the stock solution of the dialysate to the liquid replenishment channel 53; and a pressure sensor S3 that measures pressure, in this order from an upstream side on the water supply source side. On a downstream side of the pressure sensor S3, the liquid replenishment channel 53 branches toward the first and second dialysate chambers 51, 52, and liquid replenishment valves V5, V6 controlled by the control device are provided respectively in the channels thus branched.

The other end of the first bypass channel 57 is connected to the discharge channel 56, with a seventh valve V7 controlled by the control device being provided in the middle. Furthermore, a second bypass channel 60 is provided between an upstream side of the seventh valve V7 and the dialysate collection channel 55, the second bypass channel 60 being provided with an eighth valve controlled by the control device.

The dialysate stock solution supply device 59 supplies an A stock solution and a B stock solution, which are raw materials of the dialysate, by predetermined amounts to the supply chambers 51a, 52a of the first and second dialysate chambers 51, 52 via the liquid replenishment channel 53.

An upstream portion of the dialysate supply channel 54 branches in two directions and is connected to the supply chambers 51a, 52a of the first and second dialysate chambers 51, 52 respectively. A downstream-side end portion of the dialysate supply channel 54 is connected to the lower-side end portion of the dialyzer 2 in FIG. 1, to be' communicatively connected to the dialysate chamber 2b.

The branched portions of the dialysate supply channel 54 are respectively provided with supply valves V9, V10. Downstream-side portions of the branched portions are each provided with: a filter F that adsorbs endotoxin and the like in the dialysate; a sensor S4 that measures concentration and temperature of the dialysate; the infusion channel 41B used for infusion during treatment; the retransfusion channel 23B for retransfusion after the treatment; a flowmeter 61 that measures a flow rate of the dialysate; a third bypass channel 62 that is connected between the dialysate supply channel 54 and the dialysate collection channel 55; and an eleventh valve V11 controlled by the control device, in this order from the upstream side.

The infusion channel 41B is provided to be branched out from the dialysate supply channel 54 in a position on a downstream side of the sensor S4. In an end portion of the infusion channel 41B, the second connection port P2, which is arranged on the front face of the main body portion 5 in FIG. 1, is provided, to which the infusion channel 41A of the blood circuit 3 is connected as described above.

In addition, first and second flow rate adjustment valves MV1, MV2 are provided respectively in: a position on a downstream side of the branched position in the dialysate supply channel 54; and a position on a downstream side of the connection position of the infusion channel 41.

The infusion channel 41 is further provided with a twelfth valve V12 controlled by the control device, between the second flow rate adjustment valve MV2 and the second connection port P2.

During the dialysis treatment, the infusion channel 41B of the dialysate circuit 4 and the infusion channel 41A of the blood circuit 3 are connected via the second connection port P2 to configure the infusion channel 41; the twelfth valve V12 is opened; and the flow rate by the first and second flow rate adjustment valves MV1, MV2 is adjusted, whereby the dialysate is allowed to flow from the infusion channel 41 to the blood circuit 3, for infusion in a patient.

The retransfusion channel 23B is provided to be branched out from the dialysate supply channel 54 between the infusion channel 41B and the flowmeter 61. In an end portion of the retransfusion channel 23B, the first connection port P1, which is provided on the front face of the main body portion 5 in FIG. 1, is provided, to which the retransfusion channel 23 of the blood circuit 3 is connected as described above. In addition, the retransfusion channel 23 is provided with a thirteenth valve V13 controlled by the control device.

As a result, the retransfusion channel 23B of the dialysate circuit 4 and the retransfusion channel 23A of the blood circuit 3 are connected via the first connection port P1, whereby the retransfusion channel 23 as the connection channel is configured.

At the time of a retransfusion operation, by which blood in the blood circuit 3 is returned to a patient after the dialysis treatment, the thirteenth valve V13 is opened to allow the dialysate to flow from the dialysate supply channel 54 to the blood circuit 3 via the retransfusion channel 23, whereby the blood in the blood circuit 3 is pushed back to the patient.

The third bypass channel 62 branches from between the flowmeter 61 and the eleventh valve V11 to be connected to the dialysate collection channel 55, and is provided with: the fourteenth valve V14 controlled by the control device; and the priming channel 63 for circulating the dialysate from the drip chamber 9 of the blood circuit 3 during the priming operation.

In an end portion of the priming channel 63, the third connection port P3, which is provided on the front face of the main body portion 5 in FIG. 1, is provided. In addition, the priming channel 63 is provided with a twenty-fifth valve V25 controlled by the control device.

Furthermore, the second priming piping 46 is to be connected to the third connection port P3, leading to the overflow channel 45 connected to the drip chamber 9 of the blood circuit 3 as described above.

During the dialysis treatment, the third connection port P3 of the priming channel 63 is not used, with the connector 27 being closed with the lid member 28.

At the time of the priming operation, the second priming piping 46 is connected between the overflow channel 45 of the drip chamber 9 and the third connection port P3, and the fourteenth valve V14 of the third bypass channel 62 is closed, whereby the dialysate having flowed into the drip chamber 9 is discharged to the dialysate collection channel 55 of the dialysate circuit 4.

An upstream-side end portion of the dialysate collection channel 55 is connected to the dialyzer 2, on the upper side in FIG. 1. The dialysate collection channel 55 is provided with: the fifteenth valve V15 controlled by the control device; a sensor S5 that measures pressure, concentration, and temperature; an air removal tank 64 that removes air bubbles in the dialysate; the second bypass channel 60 communicatively connected to the first bypass channel 57; a dialysate pump 65 that feeds the dialysate; a water removal channel 66 for removing water during treatment; and a pressure sensor S6 that measures pressure, in this order from the dialyzer 2 side.

In addition, the dialysate collection channel 55 branches in two directions on a downstream side of the pressure sensor S6 and is connected respectively to the collection chambers 51$b$, 52$b$ of the first and second dialysate chambers 51, 52, with collection valves V16, V17 being provided respectively in the branched portions.

The air removal tank 64 is provided with an exhaust channel 67 leading to the discharge channel 56, the exhaust channel 67 being provided with an eighteenth valve V18 controlled by the control device. The air removal tank 64 is conventionally well-known, and configured to, once the used dialysate flows thereinto during the dialysis treatment, separate gas contained in the used dialysate and discharges the gas from the discharge channel 56 via the exhaust channel 67.

The second bypass channel 60 is connected to a position between the air removal tank 64 and the dialysate pump 65. The other end portion of the second bypass channel 60 is connected to an upstream side of the seventh valve V7 in the first bypass channel 57 as described above. At the time of the priming operation, the second bypass channel 60 is used for replenishing the dialysate collection channel 55 with the purified water.

The water removal channel 66 is connected to a downstream side of the dialysate pump 65, and provided with a water removal pump 68.

By activating the water removal pump 68 during the dialysis treatment, differential pressure is generated between the dialysate chamber 2$b$ and the blood chamber 2$a$ in the dialyzer 2, whereby moisture in the blood is removed.

As the liquid replenishment pump 58 and the dialysate pump 65 as the liquid feeding pump according to the present invention, so-called magnetic gear pumps are employed, which are conventionally well-known as disclosed in Japanese Patent No. 5999333, for example.

The magnetic gear pump is capable of feeding a greater amount of liquid compared to the tube pump as the blood pump 8 provided in the blood circuit 3, and, on the other hand, characterized in that no further feeding of liquid is possible when pressure in the channel has reached a predetermined level.

Specifically, the magnetic gear pump is configured to feed a liquid by means of two engaging gears, and to prevent the pressure of a channel configuring a downstream-side portion of the pump from exceeding a predetermined level, in such a way that, when the pressure has reached a predetermined level, the gears idle and are incapable of feeding a liquid.

In other words, in the case of employing the magnetic gear pump, even when the channel of the downstream-side portion of the pump is closed, it is possible to increase the pressure of the channel to a predetermined level without damaging the channel.

To the contrary, the tube pump employed as the blood pump 8 feeds a liquid while the rotor 32 compresses the tube 33, and the portion compressed by the rotor 32 is completely blocked as described above.

Consequently, in a state in which the pressure of the channel configuring a downstream-side portion of the blood pump 8 has reached a predetermined level, if the blood pump 8 further continues operating, the pressure in the channel is excessively raised due to impossibility of letting out the liquid being fed, leading to problems such as burst and detachment of the channel.

Note that, as the liquid feeding pump provided in the dialysate circuit 4, a centrifugal pump, a plunger pump and the like may also be employed, other than the magnetic gear pump.

In the discharge channel 56, an upstream-side portion branches in two directions and is connected respectively to the collection chambers 51*b*, 52*b* of the first and second dialysate chambers 51, 52, with discharge valves V19, V20 being provided respectively in the branched portions.

In addition, the discharge channel 56 is provided with: the water removal channel 66 communicatively connected to the dialysate collection channel 55; the exhaust channel 67 communicatively connected to the dialysate collection channel 55; a twenty-first valve V21 controlled by the control device; and the first bypass channel 57 communicatively connected to the liquid replenishment channel 53, in this order from the branched portion to a downstream side.

An operation of the dialysis apparatus 1 having the above-described configuration is described hereinafter. To begin with, a feeding operation of the dialysate in the dialysate circuit 4 is described.

First, the liquid replenishment pump 58 provided in the liquid replenishment channel 53 is activated to circulate the purified water in the liquid replenishment channel 53, and the dialysate stock solution supply device 59 supplies the stock solution of the dialysate to the liquid replenishment channel 53.

For example, when the liquid replenishment valve V5 adjacent to the supply chamber 51*a* of the first dialysate chamber 51 is opened and the supply valve V9 is closed, the purified water and the stock solution flow into and are blended in the supply chamber 51*a* of the first dialysate chamber 51, whereby fresh dialysate is prepared.

At this moment, if the discharge valve V19 adjacent to the collection chamber 51*b* of the first dialysate chamber 51 is opened and the collection valve V16 is closed, as the purified water and the stock solution flow into the supply chamber 51*a*, the diaphragm deforms to reduce the capacity of the collection chamber 51*b*, whereby the used dialysate contained in the collection chamber 51*b* is discharged to the discharge channel 56.

On the other hand, in the second dialysate chamber 52, the liquid replenishment valve V6 of the supply chamber 52*a* is closed and the supply valve V10 is opened, while the collection valve V17 of the collection chamber 52*b* is opened and the discharge valve V20 is closed.

Consequently, the used dialysate having passed through the dialyzer 2 is supplied into the collection chamber 52*b* by means of the dialysate pump 65 of the dialysate collection channel 55, thus reducing the capacity of the supply chamber 52*a*, whereby the fresh dialysate contained in the supply chamber 52*a* is supplied to the dialyzer 2 via the dialysate supply channel 54.

Thereafter, through alternately opening and closing the liquid replenishment valves V5, V6, the supply valves V9, V10, the collection valves V16, V17, and the discharge valves V19, V20 of the first and second dialysate chambers 51, 52, preparation and circulation of the dialysate in the dialysate circuit 4, and collection and discharge of the dialysate having passed through the dialyzer 2 are enabled.

During the dialysis treatment, when the water removal pump 68 of the water removal channel 66 is activated at desired timing while the dialysate is circulated in the dialysate circuit 4 as described above, the used dialysate in the dialysate collection channel 55 is discharged to the discharge channel 56 via the water removal channel 66, whereby differential pressure is generated inside the dialyzer 2, enabling water removal from the blood.

In addition, by controlling the first flow rate adjustment valve MV1 provided in the dialysate supply channel 54 and the second flow rate adjustment valve MV2 provided in the infusion channel 41 at desired timing during the dialysis treatment, the dialysate in the dialysate supply channel 54 can be supplied from the infusion channel 41 to the blood circuit 3, thus enabling infusion.

And then, after the dialysis treatment, by activating the blood pump 8 provided in the blood circuit 3 in at least any one of normal rotation and reverse rotation, while the dialysate is circulated in the blood circuit 3 via the retransfusion channel 23, blood remaining in the blood circuit 3 can be retransfused to the patient.

Note that the retransfusion operation during and after the dialysis treatment is conventionally well-known, and therefore more detailed description is omitted herein.

Hereinafter, a priming method for the dialysis apparatus 1 according to the first embodiment is described.

Figure 6:
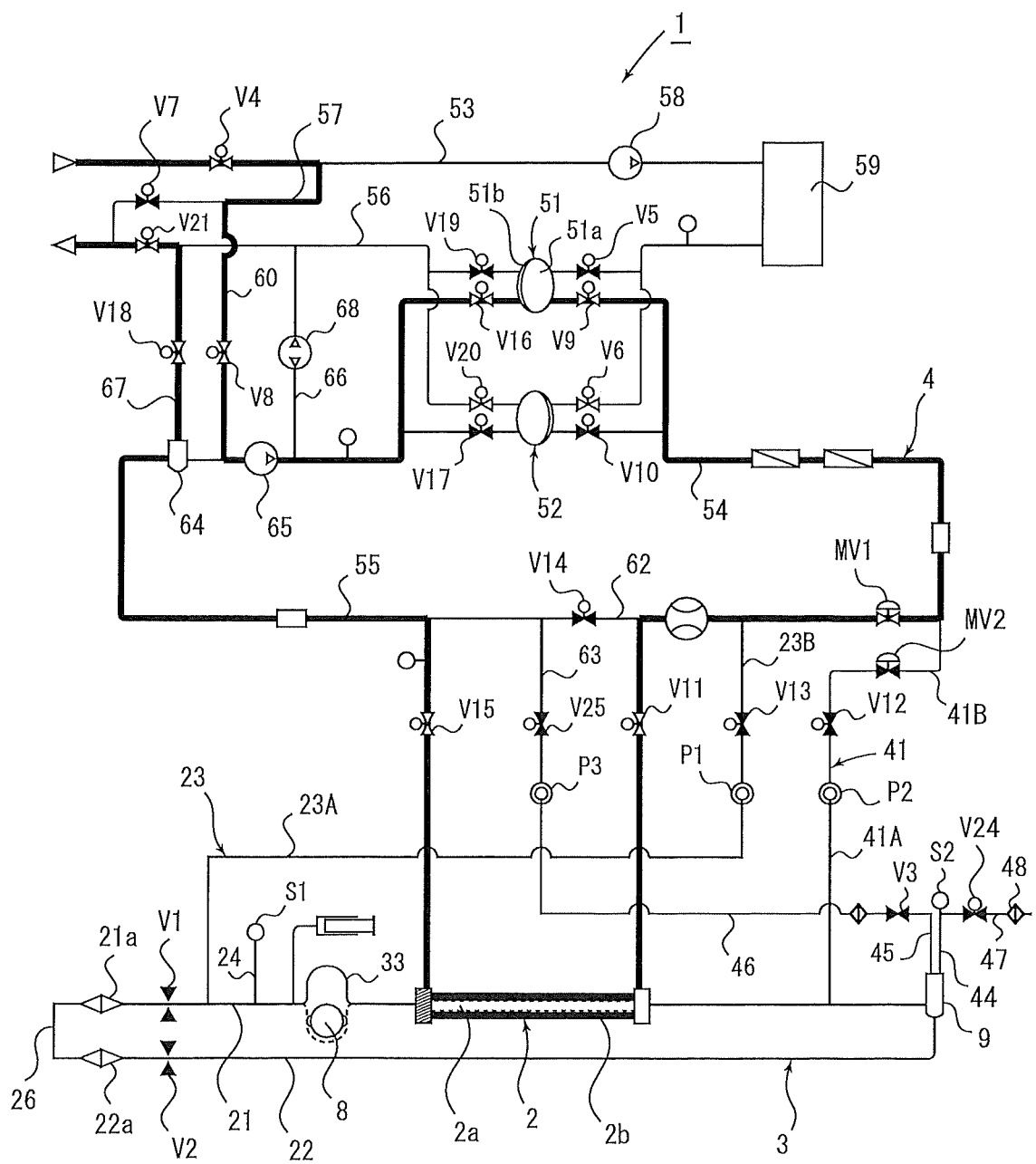
FIG. 6 is a circuit diagram illustrating a first step in the first embodiment.

FIG. 6 is a diagram illustrating a step of filling the dialysate chamber 2*b* of the dialyzer 2 with the dialysate as a first step of the priming operation, in which the dialyzer 2 and the blood circuit 3 are attached to the dialysis apparatus 1, and the dialysate circuit 4 has been filled with the dialysate in advance as shown in FIG. 1.

At this moment, the retransfusion channel 23A of the blood circuit 3 is connected to the retransfusion channel 23B of the dialysate circuit 4 via the first connection port P1, and the infusion channel 41A of the blood circuit 3 is connected to the infusion channel 41B of the dialysate circuit 4 via the second connection port P2, whereby the retransfusion channel 23 and the dialysate channel 41 as the connection channel are respectively formed.

In addition, in the blood circuit 3, the artery-side channel 21 and the vein-side channel 22 are connected by the first priming piping 26, and the second priming piping 46 is connected between the overflow channel 45 of the drip chamber 9 of the vein-side channel 22 and the third connection port P3 of the priming channel 63 in the dialysate circuit 4.

In addition, the pressure measurement channels 24, 44 provided in the artery-side channel 21 and the drip chamber 9 are also connected to the sensor ports P4, P5 of the artery-side pressure sensor S1 and the vein-side pressure sensor S2 provided on the front face of the main body portion 5, respectively.

The blood pump 8 is in the unattached state in which, as shown in FIG. 5(*a*), only the holder 34 for holding the tube 33 is attached to the holding portion 31*a* of the housing 31, and the tube 33 has not been pressed into the gap between the housing 31 and the rotor 32.

From this state, a healthcare worker gives an instruction for starting the priming operation through operating on the touch panel 6. At this moment, the dialysate is circulated in the dialysate circuit 4 by means of the first and second dialysate chambers 51, 52; however, in the following description, it is supposed that the supply valve V9 of the supply chamber 51a of the first dialysate chamber 51 and the collection valve V16 of the collection chamber 51b are opened.

In addition, in FIG. 6 and later, the parts where the dialysate circulates are shown by bold lines, and closed valves are shown by filled symbols; however, with regard to circulation of the dialysate in the dialysate circuit 4, flow of liquid caused by the priming operation is shown by bold lines, while the aforementioned bold lines for the circulation of the dialysate as the normal operation are omitted.

In the first step, the dialysate circuit 4 is already filled with the dialysate. In this state, when the dialysate pump 65 causes the dialysate in the dialysate collection channel 55 to flow into the collection chamber 51b in the first dialysate chamber 51, the diaphragm in the first dialysate chamber 51 deforms to discharge the dialysate from the supply chamber 51a.

Meanwhile, the first flow rate adjustment valve MV1 in the dialysate supply channel 54 is fully opened and the second flow rate adjustment valve MV2 in the infusion channel 41 is closed, whereby all of the dialysate being discharged circulates in the dialysate supply channel 54 and flows into the dialysate chamber 2b in the dialyzer 2.

And then, the dialysate having passed through the dialysate circuit 2 circulates in the dialysate collection channel 55 to flow into the collection chamber 51b in the first dialysate chamber 51, whereby the diaphragm is deformed to discharge the dialysate from the supply chamber 51a.

At the beginning of the priming operation, the blood chamber 2a and the dialysate chamber 2b in the dialyzer 2 are empty. Once the dialysate is circulated from the dialysate supply channel 54 to the dialyzer 2 in the first step, the dialysate chamber 2b of the dialyzer 2 is filled with the dialysate.

Therefore, the dialysate discharged from the supply chamber 51a is reduced as the dialysate chamber 2b of the dialyzer 2 is filled therewith, and even by causing the dialysate to flow into the collection chamber 51b of the first dialysate chamber 51, not all the dialysate contained in the supply chamber 51a is allowed to be discharged.

In this regard, in the first step, the seventh valve V7 of the first bypass channel 57 is closed while the eighth valve V8 of the second bypass channel 60 is opened, whereby a part of the purified water in the liquid replenishment channel 53 is circulated in the first bypass channel 57 and the second bypass channel 60, and eventually flows into the dialysate collection channel 55.

As a result, the purified water supplied from the second bypass channel 60 to the dialysate collection channel 55 flows into the collection chamber 51b of the first dialysate chamber 51, through feeding by the dialysate pump 65 operating at a predetermined flow rate.

Consequently, the lack of the dialysate flowing into the collection chamber 51b is replenished, thus enabling discharge of all the dialysate from the supply chamber 51a to the dialysate supply channel 54.

Note that, the dialysate of an amount corresponding to the amount of the extra purified water supplied from the second bypass channel 60 flows from the air removal tank 64 to the exhaust channel 67, and is then discharged from the discharge channel 56.

The first step is terminated when the dialysate pump 65 has operated at the predetermined flow rate for a predetermined period of time, or when the control device has detected that a predetermined amount of the dialysate has been fed.

Note that, each of the following second to fourth steps is also terminated when the dialysate pump 65 has operated at the predetermined flow rate for a predetermined period of time, or when the control device has detected that a predetermined amount of the dialysate has been fed.

Figure 7:
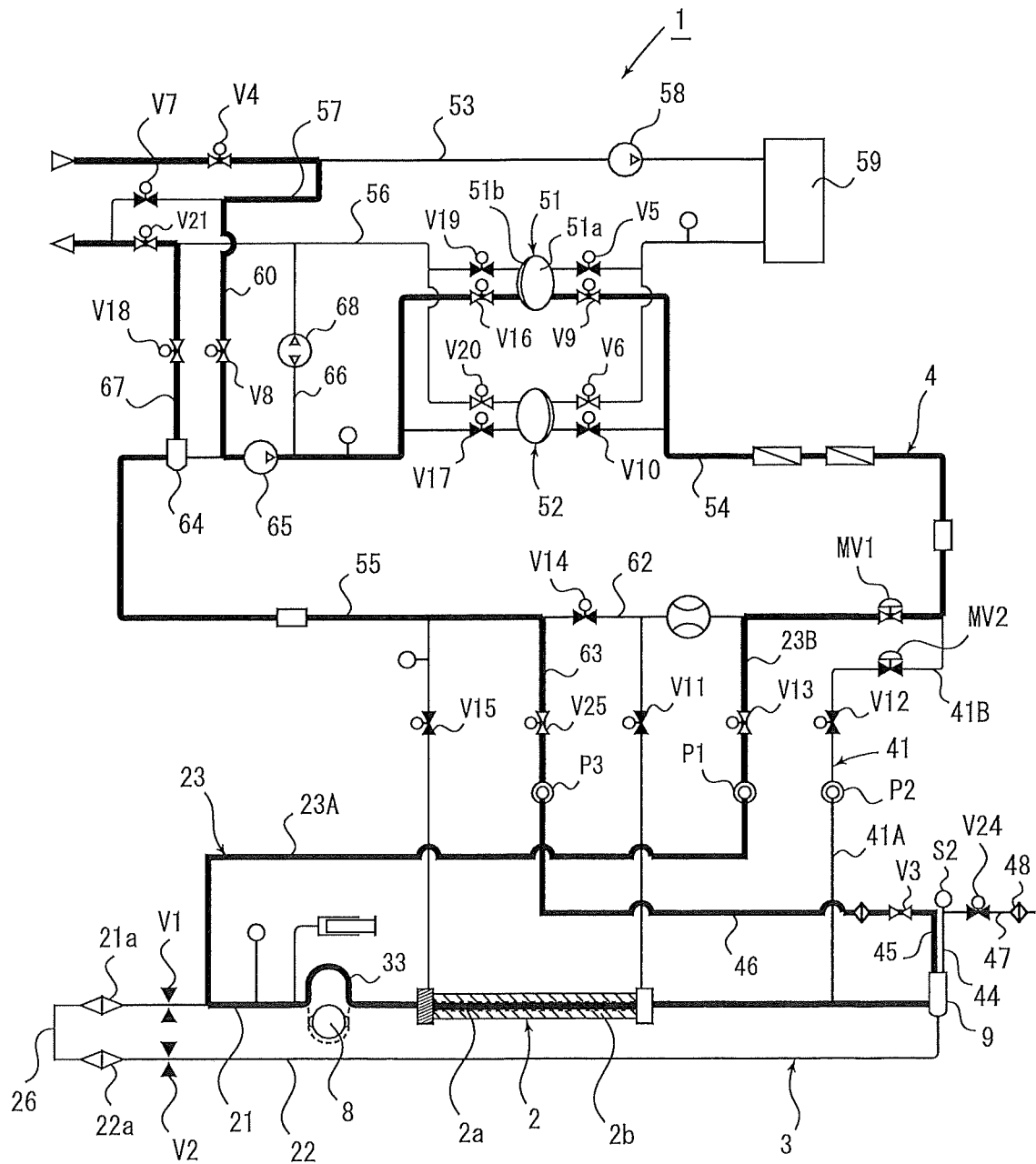
FIG. 7 is a circuit diagram illustrating a second step in the first embodiment.

In the second step shown in FIG. 7, the blood chamber 2a of the dialyzer 2, the retransfusion channel 23, a part of the artery-side channel 21, and a part of the vein-side channel 22 in the blood circuit 3 are filled with the dialysate. Note that, in FIG. 7 and later, the portions already filled with the dialysate in the previous step are shaded.

In a similar manner to the first step, the purified water is supplied from the liquid replenishment channel 53 to the dialysate collection channel 55 via the first and second bypass channels 57, 60, and the dialysate pump 65 feeds the purified water at a predetermined flow rate.

In the second step, in the dialysate circuit 4, the eleventh valve V11 of the dialysate supply channel 54 and the fifteenth valve V15 of the dialysate collection channel 55 that are adjacent to the dialyzer 2 are closed, while the twenty-fifth valve V25 of the priming channel 63 is opened.

Meanwhile in the blood circuit 3, the artery-side clamp V1 of the artery-side channel 21 and the vein-side clamp V2 of the vein-side channel 22 are closed, while the manually-operated clamp V3 of the overflow channel 45 provided in the drip chamber 9 is opened.

In addition, in the retransfusion channel 23 as the connection channel, comprising the retransfusion channel 23A of the blood circuit 3 and the retransfusion channel 23B of the dialysate circuit 4 connected via the first connection port P1, the thirteenth valve V13 is opened.

As a result, the dialysate discharged from the supply chamber 51a of the first dialysate chamber 51 of the dialysate circuit 4 flows from the dialysate supply channel 54 into the artery-side channel 21 of the blood circuit 3 via the retransfusion channel 23.

At this moment, since the blood pump 8 is in the unattached state of the tube 33, the dialysate is permitted to circulate in the tube 33. The dialysate is thus circulated from the position where the retransfusion channel 23 is connected, past the blood pump 8, toward the dialyzer 2, and flows into the blood chamber 2a of the dialyzer 2.

The dialysate thus having passed through the dialyzer 2 circulates in the vein-side channel 22 and flows into the drip chamber 9, and, with the clamp V3 being opened, circulates in the overflow channel 45 and the second priming piping 46, to flow into the priming piping 63 of the dialysate circuit 4.

At this moment, since the fourteenth valve V14 of the third bypass channel 62 is closed, the dialysate flows into the dialysate collection channel 55, and excessive dialysate is discharged from the discharge channel 56 via the air removal tank 64 and the exhaust channel 67.

In this regard, the priming carried out by circulating the dialysate in the blood circuit 3 involves a problem of removal of air bubbles in the dialyzer 2.

Conventionally, circulation of dialysate for a predetermined period of time has been practiced for removal of air bubbles. In this case, an extended period of time is required for the priming operation, thus reducing efficiency.

Given this, in the dialysis apparatus 1 according to the present embodiment, a so-called water hammer phenomenon is caused in the channels to remove air bubbles by means of an impact of hydraulic pressure.

More specifically, in the second step and the third step described later, when the dialysate is being fed to the blood circuit 3 via the retransfusion channel 23, the thirteenth valve V13 provided in the retransfusion channel 23 is opened and closed at predetermined time intervals.

When the thirteenth valve V13 is closed, internal pressure is increased in the channel on the upstream side of the thirteenth valve V13 including the retransfusion channel 23, and then, when the thirteenth valve V13 is opened in this state, the pressure thus increased is released at once to cause a so-called water hammer phenomenon, whereby shock wave enables removal of air bubbles, which are likely to be formed in the hollow fibers 12 comprised in the dialyzer 2 and especially in the cap 13 of the dialyzer 2.

At this moment, the internal pressure in the channel on the upstream side of the thirteenth valve V13 in the retransfusion channel 23 is increased in such a way that the dialysate pump 65 provided in the dialysate collection channel 55 supplies the dialysate to the collection chamber 51b of the first dialysate chamber 51, to thereby push out the dialysate from the supply chamber 51a.

In other words, the internal pressure in the retransfusion channel 23 is increased by a magnetic gear pump configuring the dialysate pump 65; however, the magnetic gear pump prevents from feeding at a pressure greater than or equal to a predetermined level, as described above.

Therefore, even when the thirteenth valve V13 is closed for causing the water hammer phenomenon, the internal pressure is increased in the channel on the upstream side of the thirteenth valve V13 including the retransfusion channel 23 will not be excessively increased, whereby burst and detachment of these channels are prevented.

Figure 8:
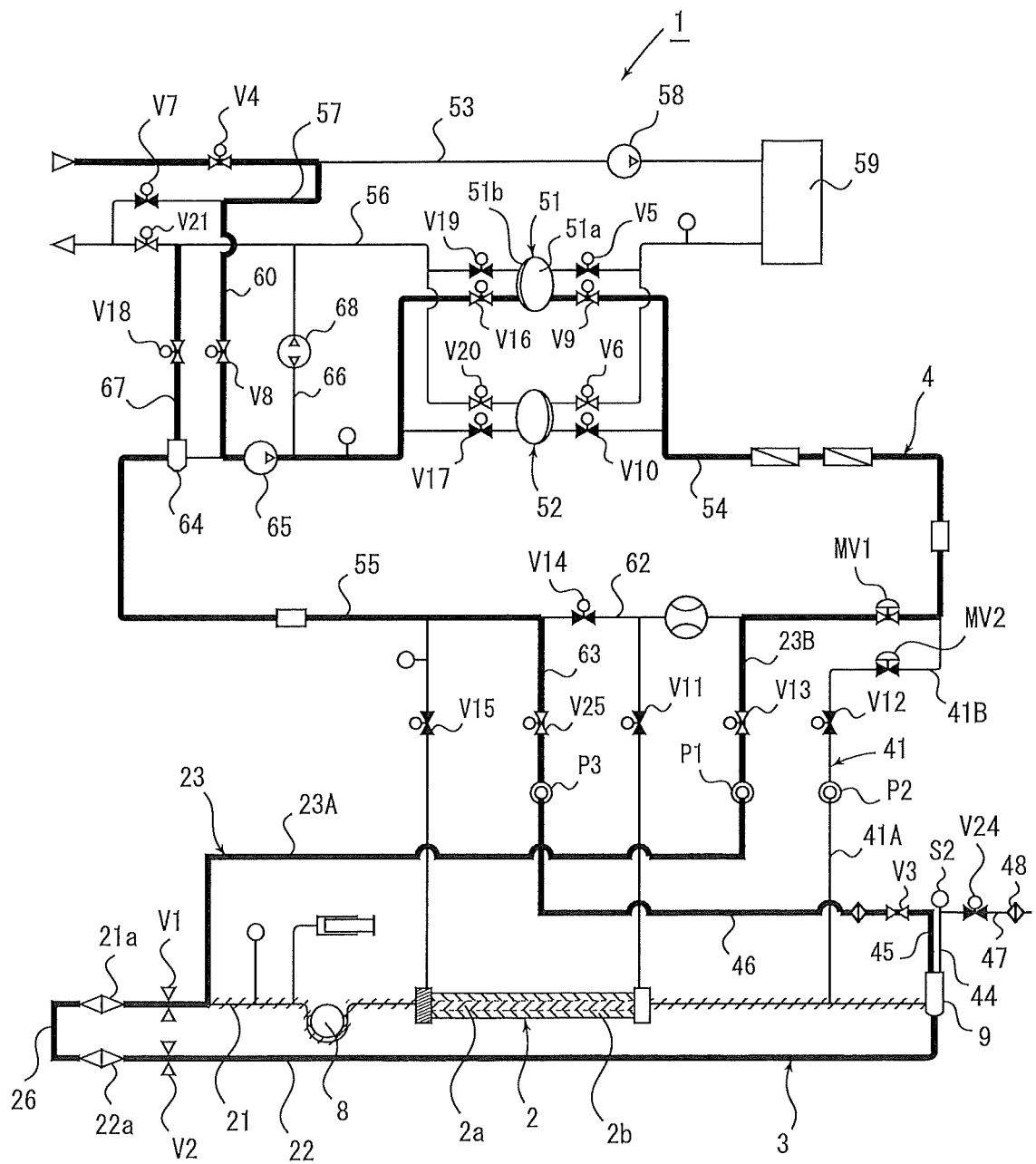
FIG. 8 is a circuit diagram illustrating a third step in the first embodiment.

In the third step shown in FIG. 8, the rest of the artery-side channel 21 and the rest of the vein-side channel 22 are filled with the dialysate.

In the third step, the artery-side clamp V1 of the artery-side channel 21 and the vein-side clamp V2 of the vein-side channel 22 are opened; the blood pump 8 of the blood circuit 3 is activated; the attached state shown in FIG. 5(c) is obtained; and in this state, the blood pump 8 is stopped.

As a result, as in the second step, the dialysate circulates in the retransfusion channel 23 and then flows into the artery-side channel 21 of the blood circuit 3; however, since the tube 33 is compressed by the rotor 32 in the blood pump 8, the dialysate circulates toward the connector 21a of the artery-side channel 21, without being able to circulate past the blood pump 8.

Thereafter, the dialysate flows from the artery-side channel 21 into the vein-side channel 22 via the first priming piping 26, circulates in the overflow channel 45 of the drip chamber 9 and in the second priming piping 46, and then flows from the priming channel 63 of the dialysate circuit 4 into the dialysate collection channel 55.

In the third step as well, in a similar manner to the second step, removal of air bubbles is enabled through the water hammer phenomenon caused by opening and closing the thirteenth valve V13 of the retransfusion channel 23 at predetermined time intervals.

Note that the blood pump 8 may be put into the attached state by a healthcare worker pulling out a handle, not illustrated, built in the rotor 32 and manually rotating the handle, without using the tube attachment device of the blood pump 8.

Figure 9:
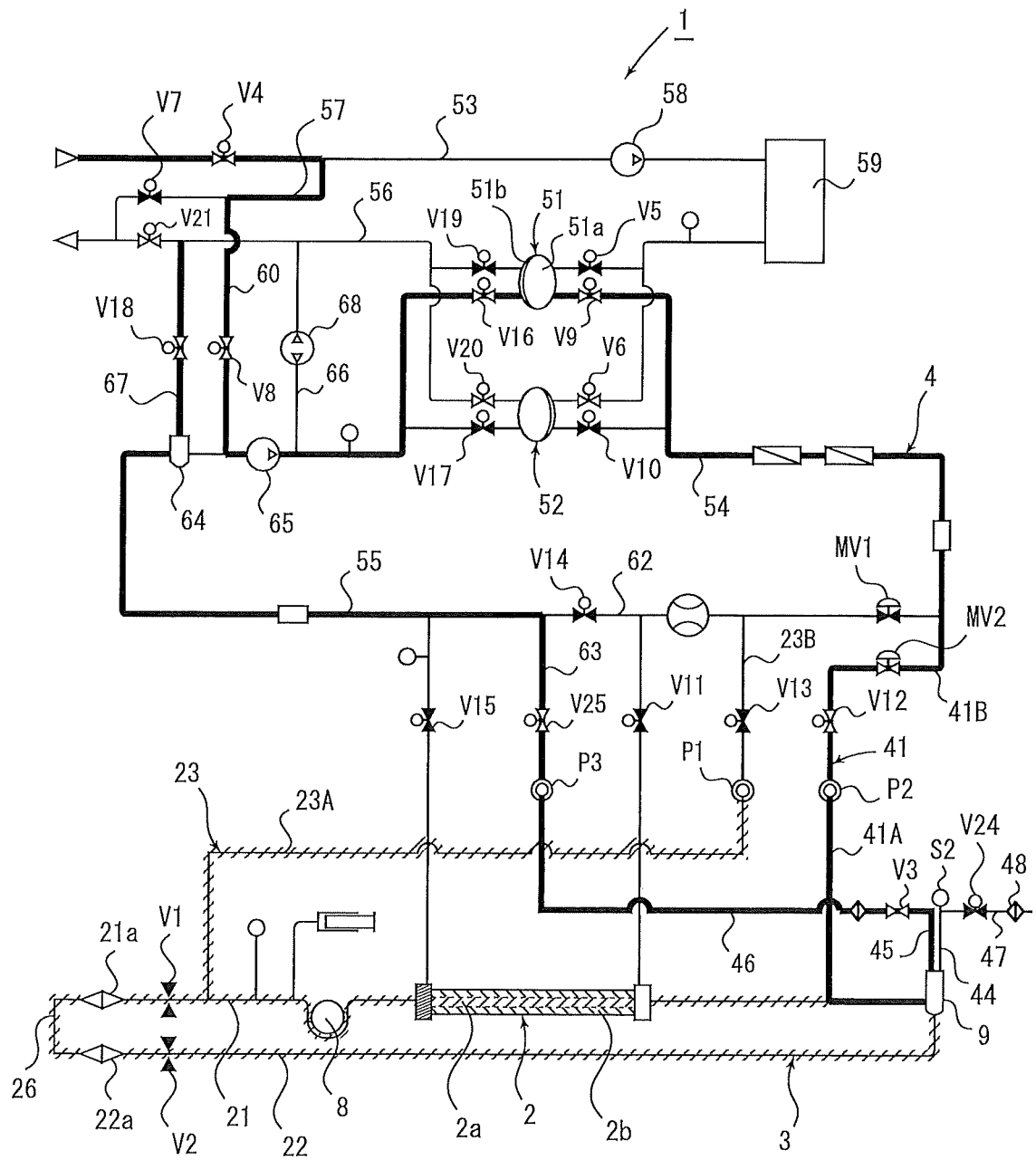
FIG. 9 is a circuit diagram illustrating a fourth step in the first embodiment.

In the fourth step shown in FIG. 9, the priming of the infusion channel 41 is carried out.

The control device closes the first flow rate adjustment valve MV1 of the dialysate circuit 4, opens the second flow rate adjustment valve MV2 of the infusion channel 41, and opens the twelfth valve V12 of the infusion channel 41.

As a result, the dialysate flows from the dialysate supply channel 54 into the infusion channel 41, and then flows into the vein-side channel 22 of the blood circuit 3.

At this moment, since the blood pump 8 is in the attached state in which the tube 33 is compressed by the rotor 32, the dialysate having flowed into the vein-side channel 22 circulates toward the drip chamber 9, not toward the dialyzer 2.

Thereafter, in a similar manner to the second and third steps, the dialysate circulates in the drip chamber 9, the overflow channel 45, the second priming piping 46, and the priming channel 63, and then flows into the dialysate circuit 4.

By carrying out the first to fourth steps as described above, the blood circuit 3 is entirely filled with the dialysate and thus the priming operation is terminated.

Thereafter, a healthcare worker removes the first priming piping 26 from the artery-side channel 21 and the vein-side channel 22 in the blood circuit 3, and removes the second priming piping 46 connected to the overflow channel 45 of the drip chamber 9.

Furthermore, the healthcare worker operates the manually-operated clamp V3 of the overflow channel 45 connected to the drip chamber 9, removes the other end of the second priming piping 46 from the third connection port P3, and closes the lid member 28 of the third connection port P3.

In addition, prior to the start of the dialysis treatment, the healthcare worker operates on the touch panel 6 to activate the twenty-fourth valve V24 of the liquid level adjustment channel 47 connected to the pressure measurement channel 44, to adjust the liquid level in the drip chamber 9.

As described above, in the dialysis apparatus 1 according to the present embodiment, the dialysate as the priming liquid is fed by using the dialysate pump 65 as the liquid feeding pump provided in the dialysate circuit 4.

Since the dialysate pump 65 is capable of feeding a greater amount of liquid compared to the tube pump employed as the blood pump 8, efficient feeding of the dialysate to the blood circuit 3 and in turn the rapid priming operation are enabled.

In the second and third steps, efficient removal of air bubbles in the blood circuit 3 is enabled through the water hammer phenomenon caused by opening and closing the thirteenth valve V13 provided in the retransfusion channel 23 at predetermined time intervals.

In this regard, since a magnetic gear pump is employed as the dialysate pump 65, the internal pressure in the retransfusion channel 23 will not be excessively increased, whereby prevention of damage and detachment of the channels comprised in the dialysate circuit is enabled.

Note that, in the first embodiment, also during circulation of the dialysate in the infusion channel 41 in the fourth step, removal of air bubbles through the water hammer phenomenon is enabled by opening and closing the twelfth valve V12.

FIGS. 10 to 14 show the priming operation of the dialysis apparatus 1 according to the second embodiment. Note that, in the configuration of the dialysis apparatus 1, description of the configurations in common with the first embodiment is omitted.

In the dialysate circuit 4 in the dialysis apparatus 1 according to the second embodiment, a fifth bypass channel 71 communicatively connected to the water removal pump 68 provided in the water removal channel 66 is provided in the dialysate stock solution supply device 59 in the liquid replenishment channel 53, and a twenty-second valve V22 opened and closed by the control device is provided in the fifth bypass channel 71.

Furthermore, in the present embodiment, at the time of the priming operation, third and fourth priming pipings 72, 73 are to be connected, instead of the first and second priming pipings 26, 46 in the first embodiment.

The third priming piping 72 is connected between the connector of the retransfusion channel 23A provided on the artery-side channel 21 of the blood circuit 3 and the connector 22a of the vein-side channel 22. The fourth priming piping 73 is connected between the connector 21a of the artery-side channel 21 and the third connection port P3 of the priming channel 63 in the dialysate circuit 4.

Figure 10:
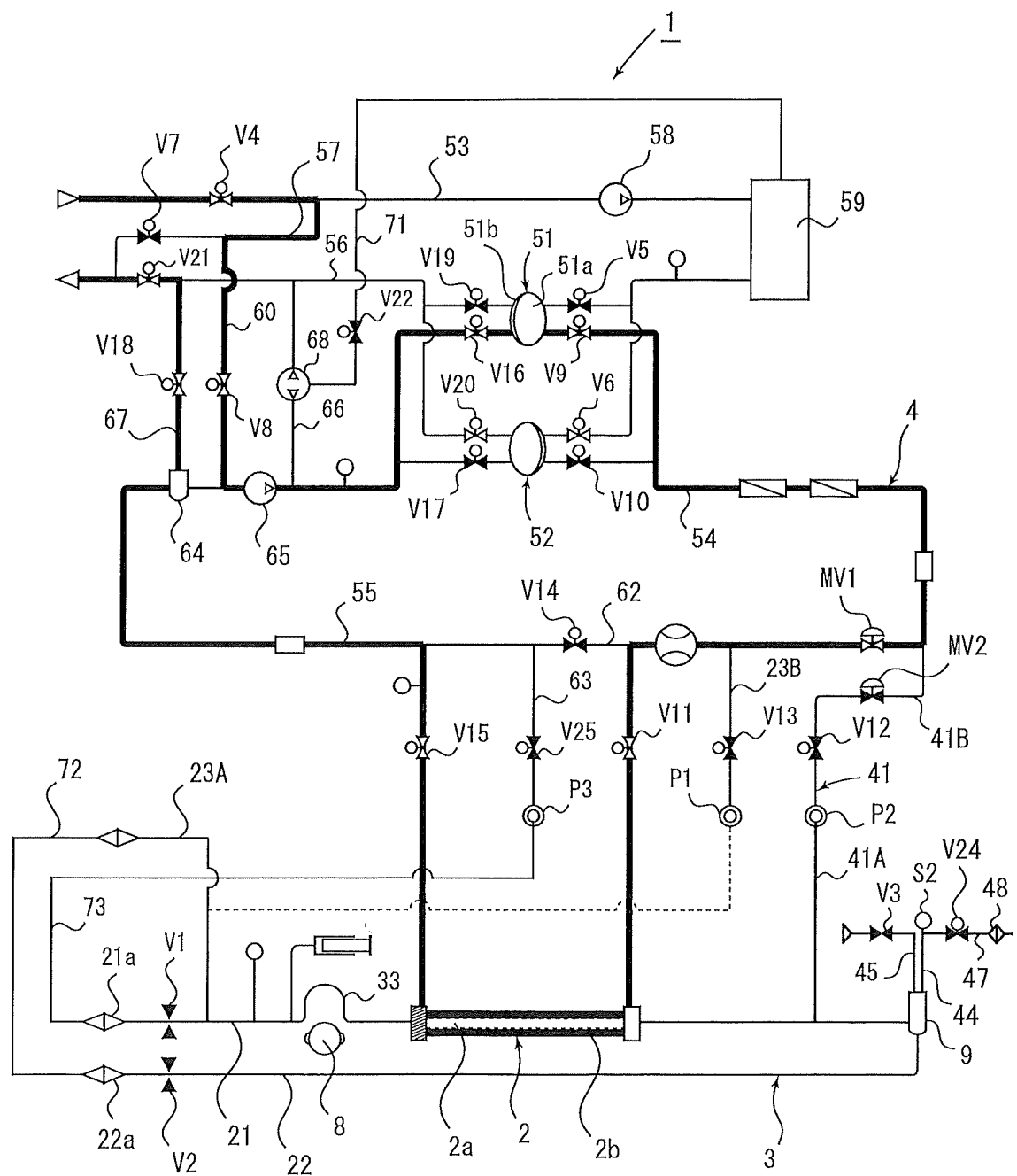
FIG. 10 is a circuit diagram illustrating a first step in a second embodiment.

Hereinafter, a priming method for the dialysis apparatus 1 according to the second embodiment is described. FIG. 10 shows a first step in which operations similar to those of the first step of the first embodiment shown in FIG. 6 are carried out.

In other words, in the first step, while the dialysate is circulated in the dialysate circuit 4, the purified water in the liquid replenishment channel 53 is allowed to flow into the dialysate collection channel 55 via the first bypass channel 57 and the second bypass channel 60, whereby the dialysate chamber 2b of the dialyzer 2 is filled with the dialysate, while the dialysate being lost for filling the dialysate chamber 2b is replenished.

In a similar manner to the first embodiment described above, the first step is terminated when the dialysate pump 65 has operated at the predetermined flow rate for a predetermined period of time, or when the control device has detected that a predetermined amount of the dialysate has been fed.

Note that, each of the following second, third, and fifth steps of the second embodiment is also terminated when the dialysate pump 65 has operated at the predetermined flow rate for a predetermined period of time, or when the control device has detected that a predetermined amount of the dialysate has been fed.

Figure 11:
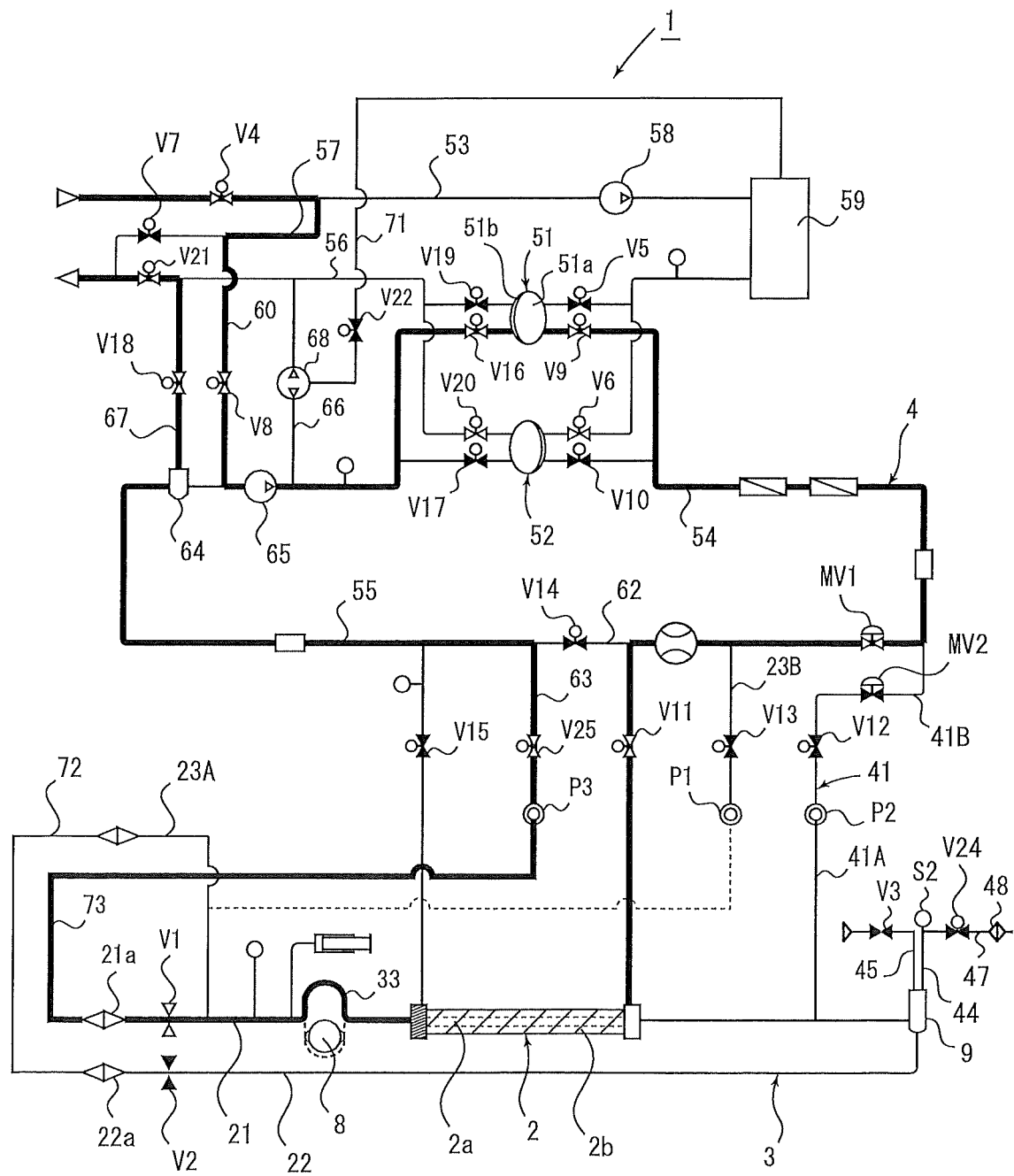
FIG. 11 is a circuit diagram illustrating a second step in the second embodiment.

FIG. 11 shows the second step. In the second step, the dialysate is allowed to pass from the dialysate chamber 2b of the hollow fibers 12 to the blood chamber 2a inside the dialyzer 2, and is circulated to the artery-side channel 21 of the blood circuit 3.

More specifically, the fifteenth valve V15 of the dialysate collection channel 55 is closed, the twenty-fifth valve V25 of the priming channel 63 is opened, and the artery-side clamp V1 of the artery-side channel 21 in the blood circuit 3 is opened. Meanwhile, the blood pump 8 is in the unattached state.

As a result, the dialysate supplied from the dialysate supply channel 54 flows into the dialysate chamber 2b of the dialyzer 2. Then, with the fifteenth valve V15 of the dialysate collection channel 55 and the vein-side clamp V2 of the vein-side channel 22 being closed, the dialysate passes through the hollow fibers 12 under the internal pressure and flows from the dialysate chamber 2b into the blood chamber 2a.

In addition, since the blood pump 8 is in the unattached state of the tube 33 in the blood circuit 3, the dialysate circulates in the artery-side channel 21, passes through the tube 33, and circulates past the blood pump 8.

Thereafter, the dialysate flows from the artery-side channel 21 into the fourth priming piping 73, and then flows into the priming channel 63 of the dialysate circuit 4.

Figure 12:
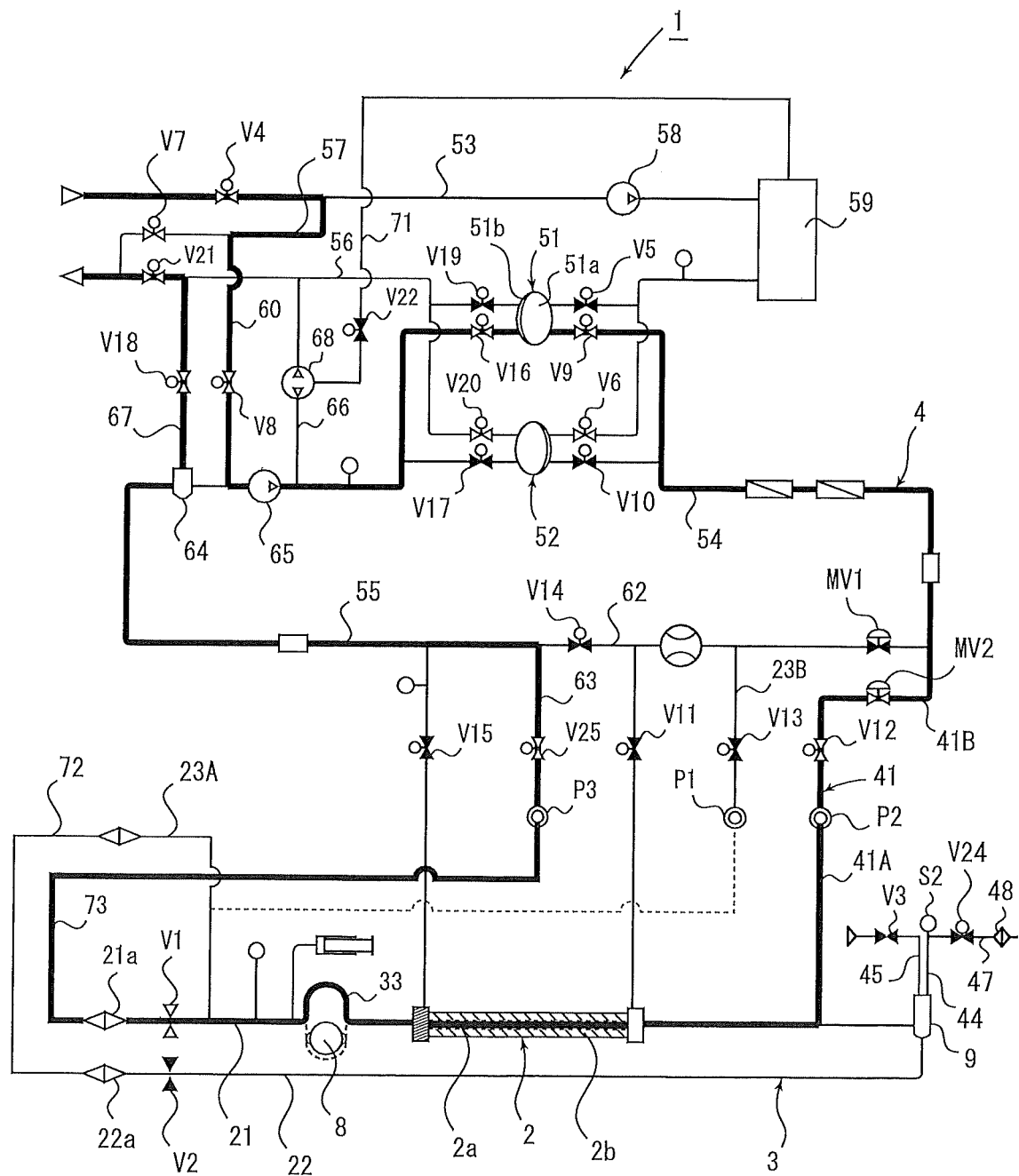
FIG. 12 is a circuit diagram illustrating a third step in the second embodiment.

FIG. 12 shows the third step. In the third step of the second embodiment, the dialysate is allowed to flow from the infusion channel 41 into the blood circuit 3, and a part of the vein-side channel 22 is filled with the dialysate.

More specifically, the first flow rate adjustment valve MV1 of the dialysate supply channel 54 is closed, and the second flow rate adjustment valve MV2 and the twelfth valve V12 of the infusion channel 41 are opened.

Meanwhile in the blood circuit 3, the blood pump 8 remains in the unattached state, and the artery-side clamp V1 of the artery-side channel 21 is opened and the vein-side clamp V2 of the vein-side channel 22 is closed.

Note that, in a similar manner to the first embodiment, a healthcare worker may manually switch the blood pump 8 from the unattached state to the attached, state.

As a result, the dialysate having flowed from the dialysate supply channel 54 into the infusion channel 41B circulates in the infusion channel 41A on the blood circuit 3 side and flows into the vein-side channel 22. With the vein-side clamp V2 of the vein-side channel 22 being closed, the dialysate passes through the blood chamber 2a of the dialyzer 2.

Since the blood pump 8 is in the unattached state of the tube 33, the dialysate circulates past the blood pump 8 in the artery-side channel 21, and then flows from the fourth priming piping 73 into the priming channel 63 of the dialysate circuit 4.

In this third step, in a similar manner to the first embodiment, removal of air bubbles in the dialyzer 2 is enabled through the water hammer phenomenon caused by opening and closing the twelfth valve V12 of the retransfusion channel 41 at predetermined time intervals.

Note that, since the range of circulation of the dialysate in the artery-side channel 21 in the third step overlaps the range of circulation of the dialysate in the second step, the second step may be omitted.

Figure 13:
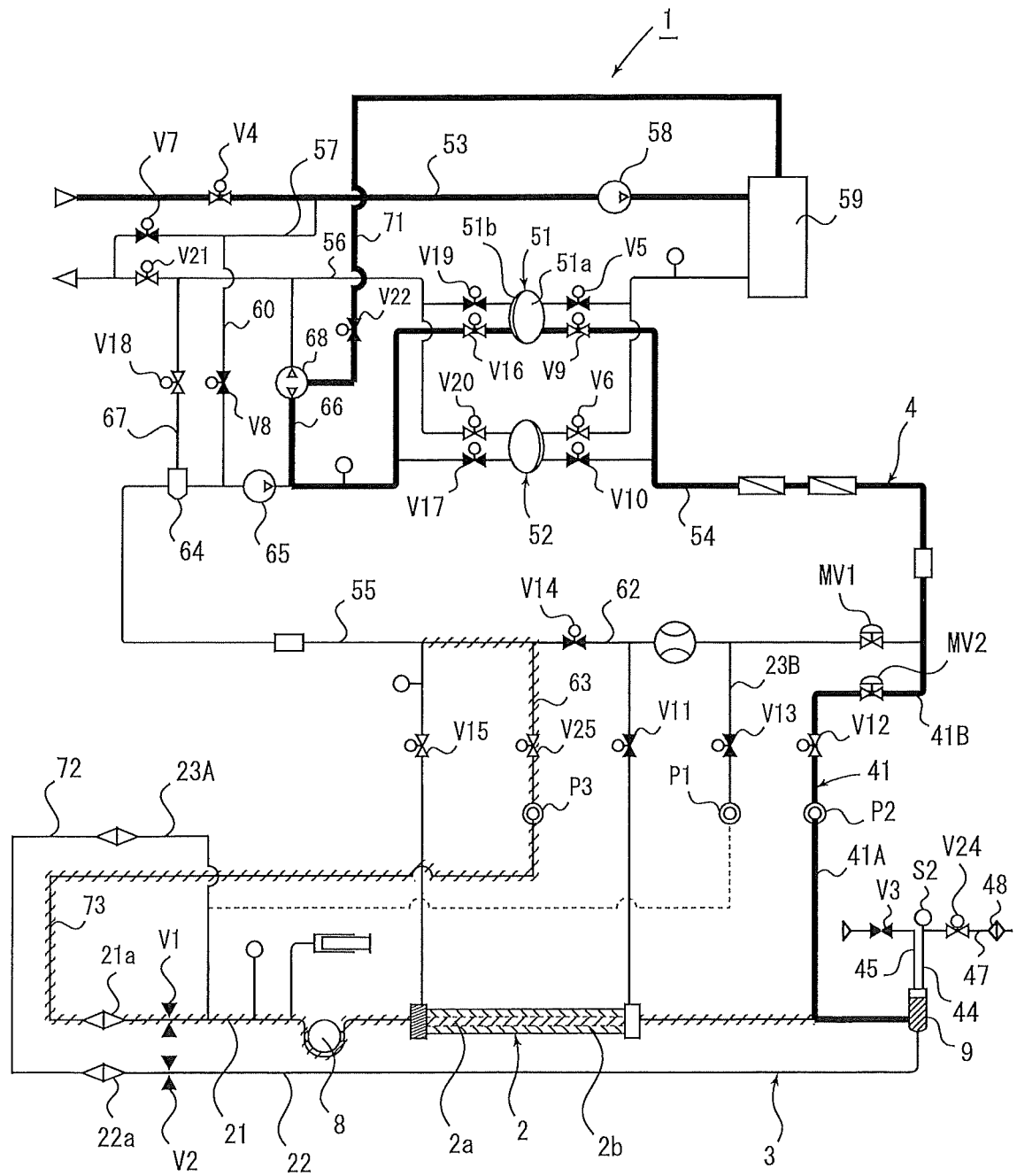
FIG. 13 is a circuit diagram illustrating a fourth step in the second embodiment.

FIG. 13 shows the fourth step. In the fourth step, the liquid level in the drip chamber 9 is adjusted.

In this fourth step, the seventh and eighth valves V7, V8 of the first and second bypass channels 57, 60 in the dialysate circuit 4 are closed, the first flow rate adjustment valve MV1 of the dialysate supply channel 54 is closed, and the second flow rate adjustment valve MV2 and the twelfth valve V12 of the infusion channel 41 are opened.

Meanwhile in the blood circuit 3, the artery-side clamp V1 of the artery-side channel 21 and the vein-side clamp V2 of the vein-side channel 22 are closed, and the clamp V3 of the overflow channel 45 in the drip chamber 9 is opened. Note that the tube 33 of the blood pump 8 may remain in the unattached state, but is in the attached state in the present embodiment.

In this state, the water removal pump 68 provided in the water removal channel 66 is activated, and the twenty-second valve V22 of the fifth bypass channel 71 is opened.

Then, the purified water is supplied from the liquid replenishment channel 53 to the dialysate collection channel 55 via the fifth bypass channel 71, whereby the collection chamber 51b of the first dialysate chamber 51 is deformed to discharge the dialysate from the supply chamber 51a.

The dialysate flows from the dialysate supply channel 54 into the vein-side channel 22 via the infusion channel 41. At this moment, since the artery-side clamp V1 of the artery-side channel 21 and the vein-side clamp V2 of the vein-side channel 22 are closed, the dialysate flows into the drip chamber 9. Meanwhile, the clamp V3 of the overflow channel 45 is closed.

The control device opens the twenty-fourth valve V24 of the liquid level adjustment channel 47 connected to the drip chamber 9, whereby air in the drip chamber 9 is to be discharged as the dialysate flows into the drip chamber 9 to raise the liquid level.

Since the water removal pump 68 feeds a smaller amount of liquid accurately, the control device can set the level of the dialysate in the drip chamber 9 appropriately through control of an operating time period of the water removal pump 68, for example.

Note that, the adjustment of the liquid level in the drip chamber 9 in the fourth step may also be carried out manually, and thus the fourth step may be omitted.

Figure 14:
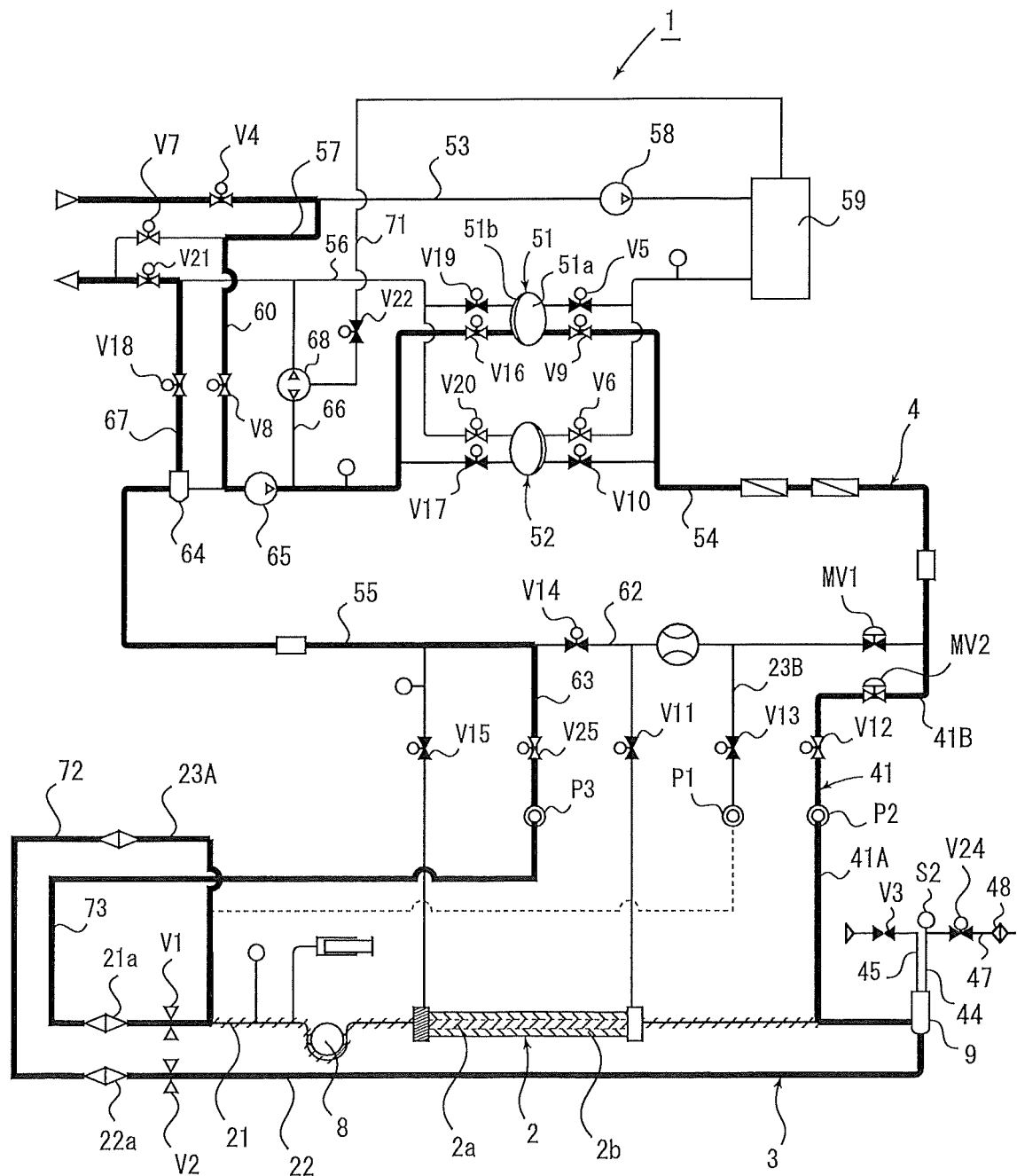
FIG. 14 is a circuit diagram illustrating a fifth step in the second embodiment.

FIG. 14 shows the fifth step. In the fifth step, the dialysate is allowed to flow via the infusion channel 41 into the blood circuit 3, and the rest of the vein-side channel 22 is filled with the dialysate.

More specifically, the water removal pump 68 used in the fourth step is stopped and the twenty-second valve of the fifth bypass channel 71 is closed, whereby, in a similar manner to the first to third steps, the purified water in the liquid replenishment channel 53 is circulated in the dialysate collection channel 55 via the first and second bypass channels 57, 60.

And then, the first flow rate adjustment valve MV1 of the dialysate supply channel 54 is closed, and the second flow rate adjustment valve MV2 and the twelfth valve V12 of the infusion channel 41 are opened.

Meanwhile in the blood circuit 3, the tube 33 of the blood pump 8 is put in the attached state, and in this state, the artery-side clamp V1 of the artery-side channel 21 and the vein-side clamp V2 of the vein-side channel 22 are opened.

As a result, the dialysate having flowed from the dialysate supply channel 54 into the infusion channel 41 circulates in the infusion channel 41 on the blood circuit 3 side to flow into the vein-side channel 22. With the blood pump 8 being in the attached state, the dialysate cannot circulate past the blood pump 8 and thus circulates toward the drip chamber 9.

In the drip chamber 9, with the clamp V3 of the overflow channel 45 and the twenty-fourth valve V24 of the liquid level adjustment channel 47 being closed, the dialysate having flowed in passes through the drip chamber 9 and then flows into the artery-side channel 21 via the third priming piping 72 and the retransfusion channel 23.

At this moment, since the blood pump 8 is in the attached state, the dialysate further flows from the artery-side channel 21 into the fourth priming piping 73, and then flows into the priming channel 63 of the dialysate circuit 4.

The priming is thus completed. Thereafter, a healthcare worker removes the third priming piping 72 from the retransfusion channel 23A, and then connects the end portion of the retransfusion channel 23A to the first connection port P1 in the retransfusion channel 23B of the dialysate circuit 4.

Although the retransfusion channel 23B is reattached after the completion of the fifth step in the second embodiment, it is also possible to connect the retransfusion channel 23A of the blood circuit 3 to the retransfusion channel 23B of the dialysate circuit 4 at the time of the priming operation, to carry out the priming of the retransfusion channel 23 in a similar manner to the first embodiment.

In this case, although not illustrated, a port to which the third priming piping 72 can be connected is provided in the artery-side channel 21 of the blood circuit 3, and the third priming piping 72 is connected to the port at the time of the priming operation.

The port is preferably positioned between the artery-side clamp V1 and the connector 21a in the artery-side channel 21. Connecting the third priming piping 72 in this position permits communicative connection between the artery-side channel 21 and the vein-side channel 23 via the third priming piping 72.

Then, at the time of the priming operation, priming manipulation of the retransfusion channel 23A and the retransfusion channel 23B, which takes place in the third step of the first embodiment shown in FIG. 8, is carried out between the second step and the third step of the second embodiment.

FIGS. 15 to 18 show the priming operation of the dialysis apparatus 1 according to the third embodiment. Note that, in the configuration of the dialysis apparatus 1, description of the configurations in common with the second embodiment is omitted.

The dialysis apparatus 1 according to the third embodiment is different from the dialysis apparatus 1 according to the second embodiment in that the connection position of the infusion channel 41A in the blood circuit 3 is in the artery-side channel 21. More specifically, the end portion of the infusion channel 41A is connected between the dialyzer 2 and the blood pump 8.

Also with the configuration of providing the infusion channel 41A in the artery-side channel 21 as described above, the dialysate may be circulated from the dialysate supply channel 54 to the artery-side channel 21 via the infusion channel 41 during the dialysis treatment, to carry out infusion.

However, due to providing the infusion channel 41A in the artery-side channel 21, the dialysate supplied from the infusion channel 41 is circulated in the dialyzer 2, and serves for dialysis between the dialysate chamber 2b and the blood chamber 2a in the dialyzer 2.

Figure 15:
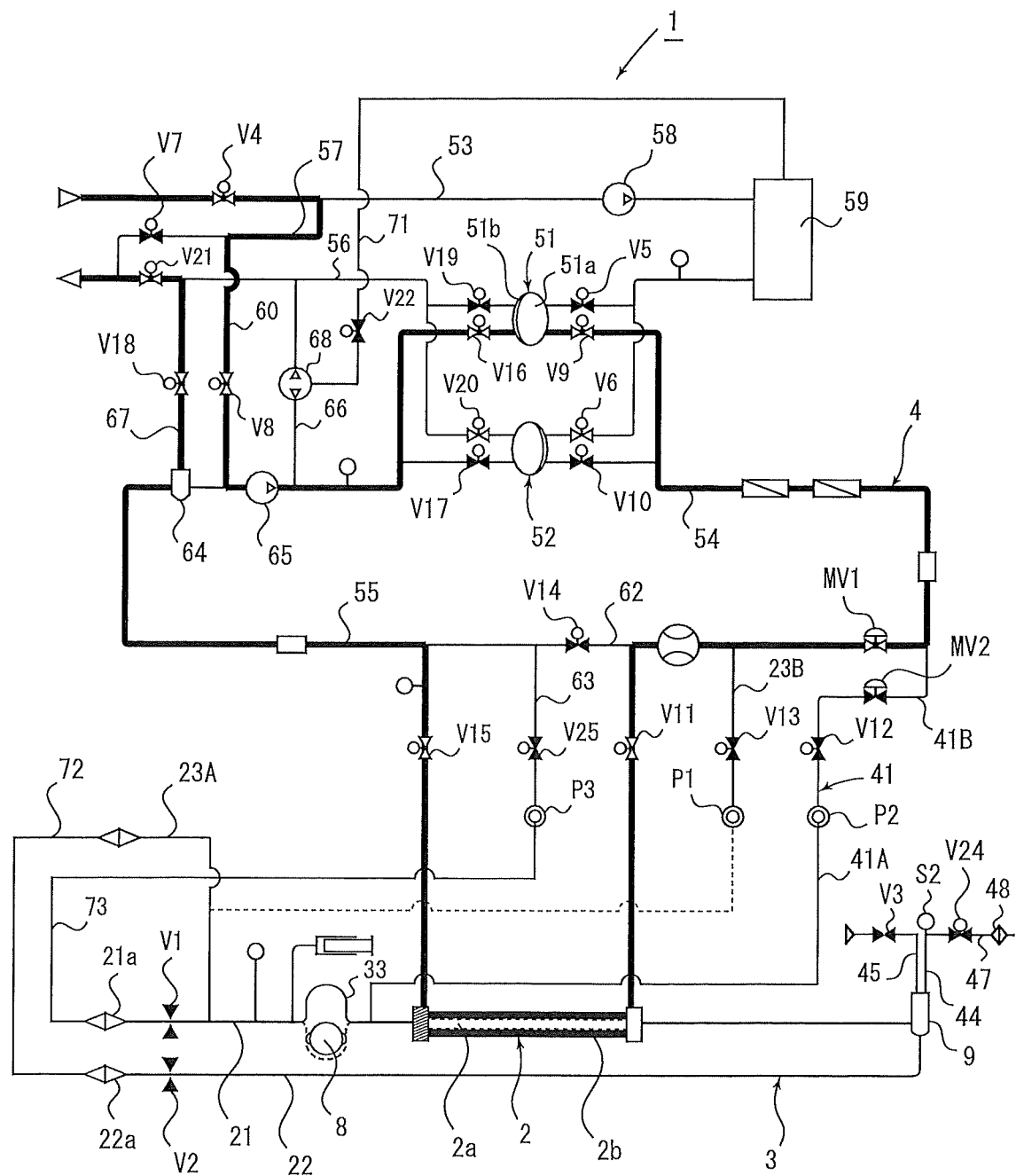
FIG. 15 is a circuit diagram illustrating a first step in a third embodiment.

Hereinafter, a priming method for the dialysis apparatus 1 according to the third embodiment is described. FIG. 15 shows a first step corresponding to the first step of the first embodiment shown in FIG. 6 and of the second embodiment shown in FIG. 10.

In other words, in the first step, while the dialysate is circulated in the dialysate circuit 4, the purified water in the liquid replenishment channel 53 is allowed to flow into the dialysate collection channel 55 via the first bypass channel 57 and the second bypass channel 60, whereby the dialysate chamber 2b of the dialyzer 2 is filled with the dialysate, while the dialysate being lost for filling the dialysate chamber 2b is replenished.

In a similar manner to the first and second embodiments described above, the first step is terminated when the control device has detected that a predetermined amount of the dialysate has been fed as a result of operating the dialysate pump 65 at the predetermined flow rate for a predetermined period of time.

Note that, each of the following second and fifth steps of the third embodiment is also terminated when the control device has detected that a predetermined amount of the dialysate has been fed as a result of operating the dialysate pump 65 at the predetermined flow rate for the predetermined period of time.

Figure 16:
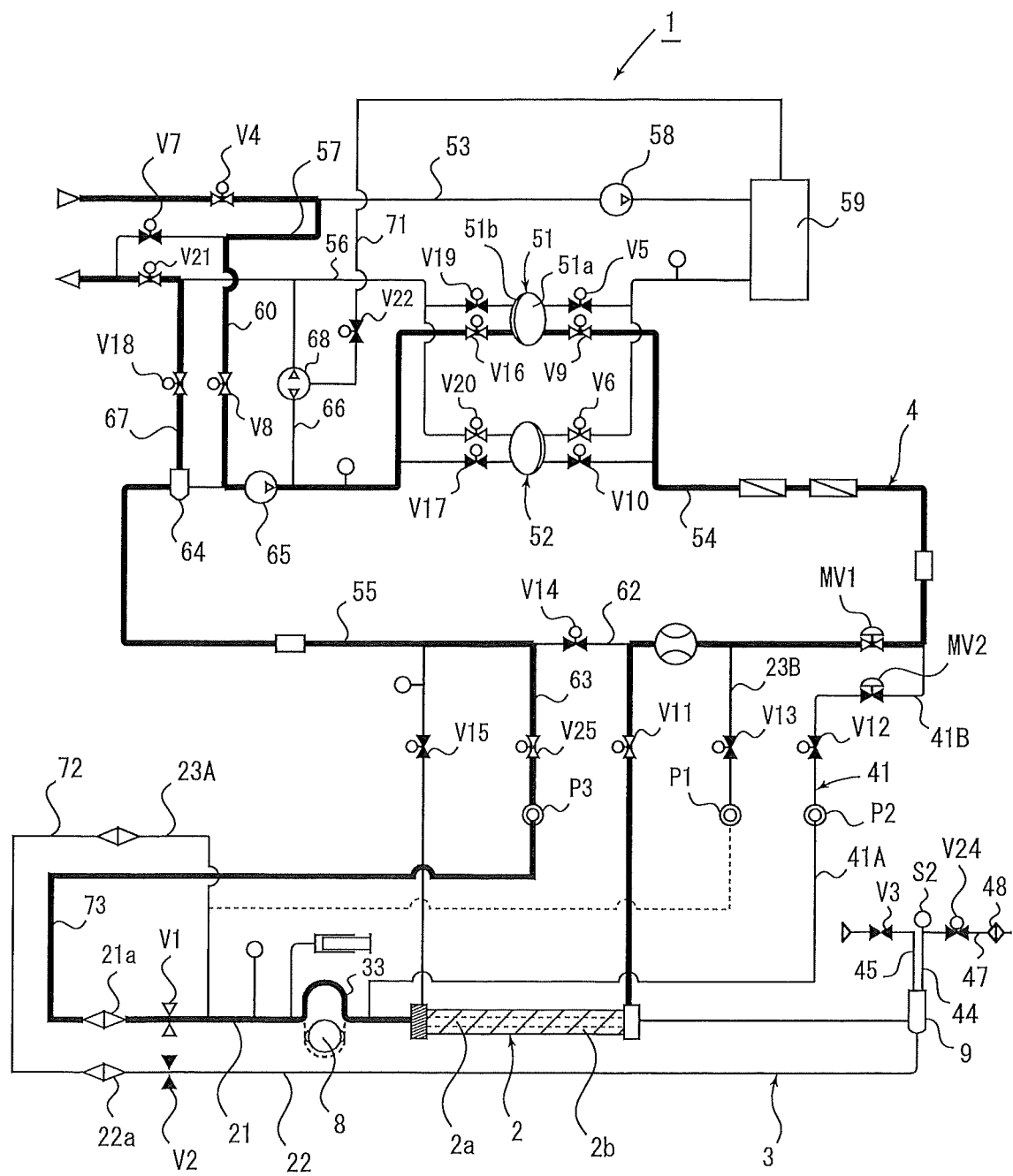
FIG. 16 is a circuit diagram illustrating a second step in the third embodiment.

FIG. 16 shows the second step. In the second step, the dialysate is allowed to pass from the dialysate chamber 2b of the hollow fibers 12 to the blood chamber 2a in the dialyzer 2, and is circulated to the artery-side channel 21 of the blood circuit 3.

More specifically, the fifteenth valve V15 of the dialysate collection channel 55 is closed, the twenty-fifth valve V25 of the priming channel 63 is opened, and the artery-side clamp V1 of the artery-side channel 21 in the blood circuit 3 is opened. Meanwhile, the blood pump 8 is in the unattached state.

As a result, the dialysate supplied from the dialysate supply channel 54 flows into the dialysate chamber 2b of the dialyzer 2. Then, with the fifteenth valve V15 of the dialysate collection channel 55 and the vein-side clamp V2 of the vein-side channel 22 being closed, the dialysate passes through the hollow fibers 12 under the internal pressure and flows from the dialysate chamber 2b into the blood chamber 2a.

In addition, since the blood pump 8 is in the unattached state in the blood circuit 3, the dialysate is permitted to circulate in the tube 33, and to circulate past the blood pump 8.

Thereafter, the dialysate flows from the artery-side channel 21 into the fourth priming piping 73, and then flows from the third connection port P3 into the priming channel 63 of the dialysate circuit 4.

Figure 17:
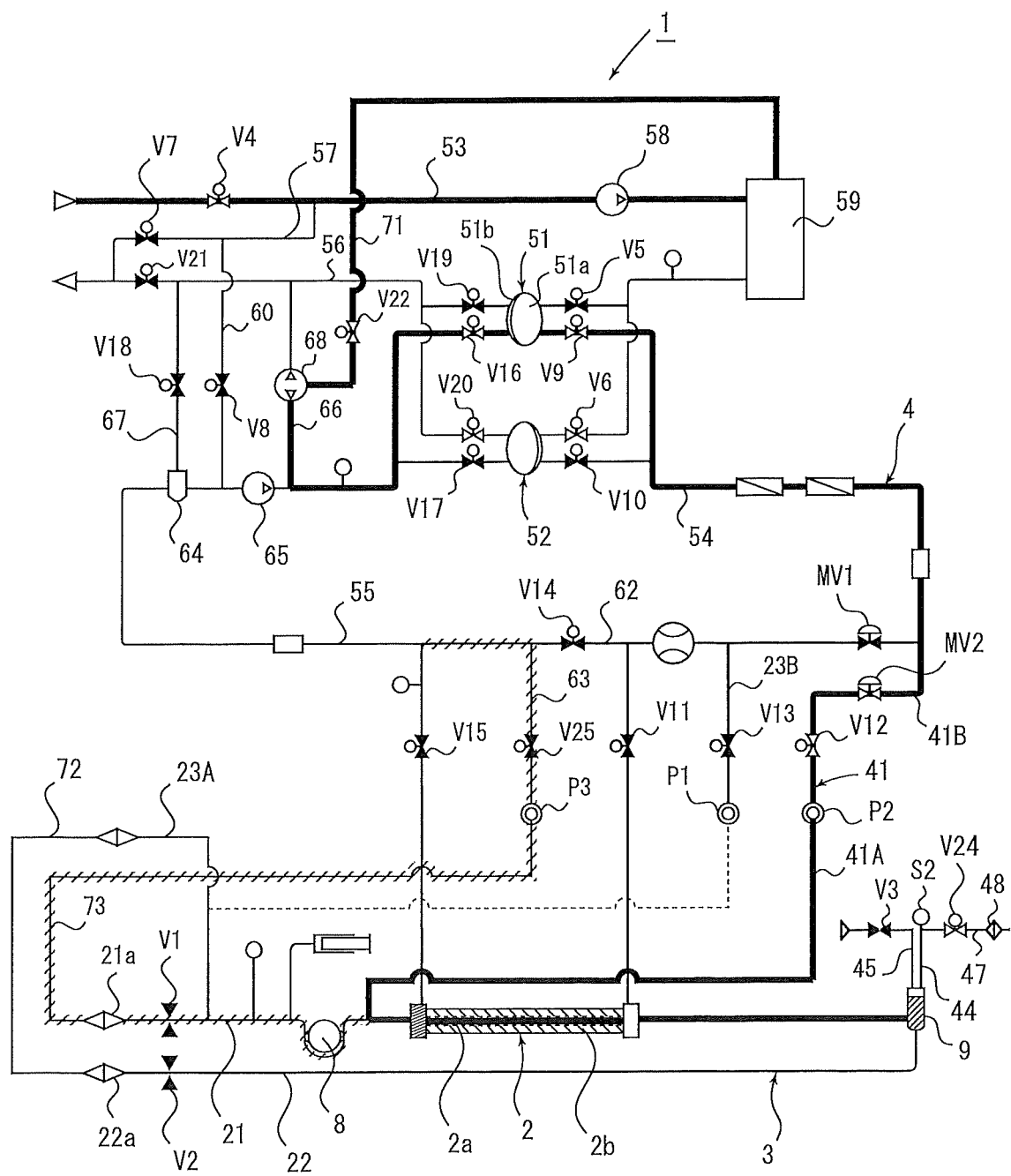
FIG. 17 is a circuit diagram illustrating a third step in the third embodiment.

FIG. 17 shows the third step. In the third step, the dialysate is allowed to flow via the infusion channel 41 into the blood circuit 3, and the liquid level in the drip chamber 9 provided on the vein-side channel 22 is adjusted.

More specifically, the first flow rate adjustment valve MV1 of the dialysate supply channel 54 is closed, and the second flow rate adjustment valve MV2 and the twelfth valve V12 of the infusion channel 41 are opened. Meanwhile in the blood circuit 3, the tube 33 of the blood pump 8 is put in the attached state, and the clamp V3 of the overflow channel 45 of the drip chamber 9 is opened.

Furthermore, in the third step, the water removal pump 68 provided in the water removal channel 66 is activated, and the twenty-second valve V22 of the fifth bypass channel 71 is opened.

As a result, the dialysate having flowed from the dialysate supply channel 54 into the infusion channel 41 circulates in the infusion channel 41 on the blood circuit 3 side to flow into the vein-side channel 21. With the blood pump 8 being in the attached state, the dialysate cannot circulate past the blood pump 8, and thus passes through the blood chamber 2a of the dialyzer 2 to flow into the vein-side channel 22.

Thereafter, the dialysate flows into the drip chamber 9, during which the dialysate is fed by the water removal pump 68 and the twenty-fourth valve V24 provided in the liquid level adjustment channel 47 is operated, whereby fine adjustment of the liquid level is enabled.

Similar to the fourth step in the second embodiment, the third step may also be omitted since the liquid level adjustment in the drip chamber 9 can be manually carried out.

Figure 18:
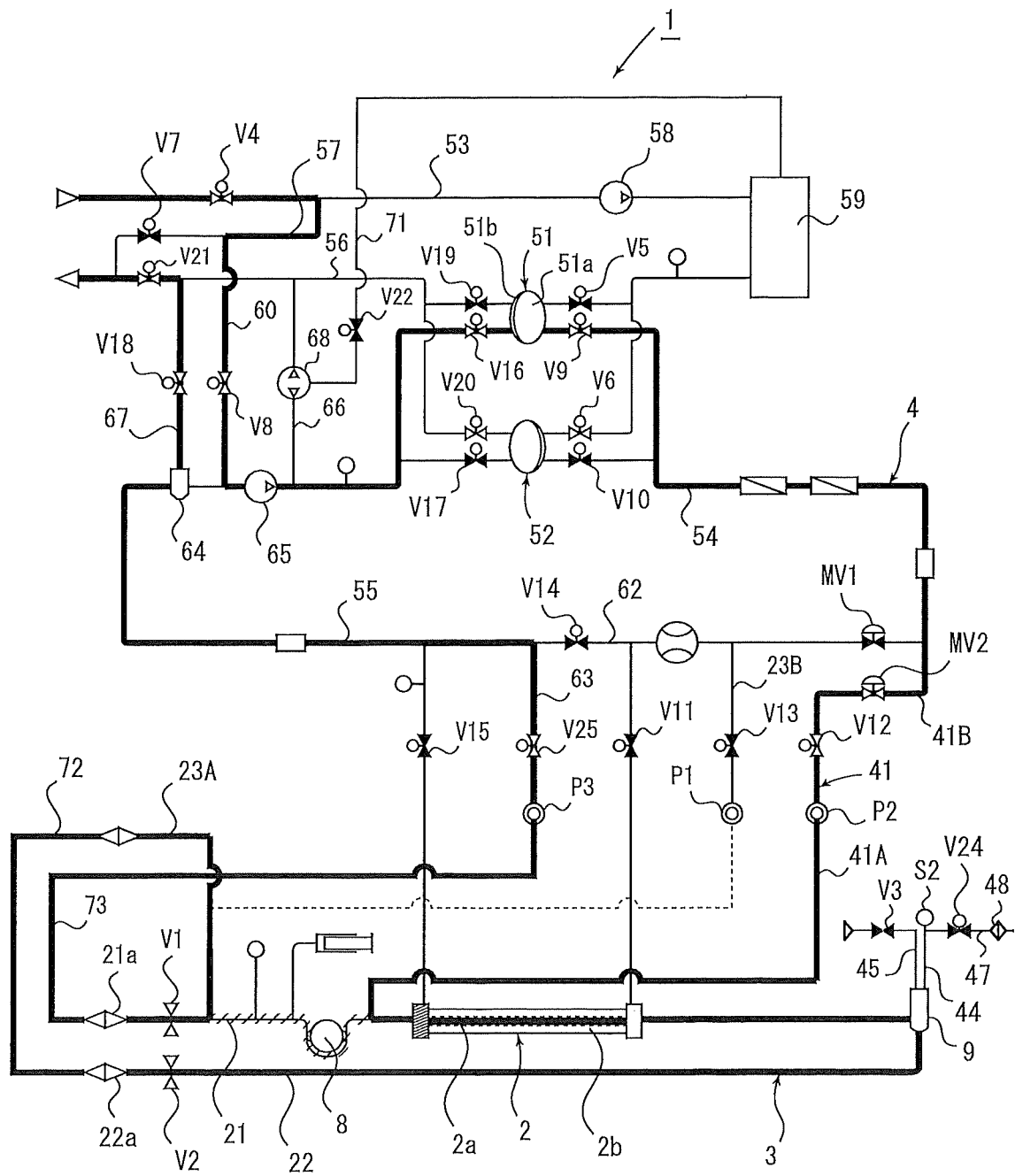
FIG. 18 is a circuit diagram illustrating a fourth step in the third embodiment.

FIG. 18 shows the fourth step. In the fourth step, the dialysate is allowed to flow via the infusion channel 41 into the blood circuit 3, and is circulated in the vein-side channel 22.

More specifically, the first flow rate adjustment valve MV1 of the dialysate supply channel 54 is closed, and the second flow rate adjustment valve MV2 and the twelfth valve V12 of the infusion channel 41 are opened.

Meanwhile in the blood circuit 3, the tube 33 of the blood pump 8 is put in the attached state, and the artery-side clamp V1 of the artery-side channel 21 and the vein-side clamp V2 of the vein-side channel 22 are opened. Furthermore, the manually-operated clamp V3 of the overflow channel 45 of the drip chamber 9 is closed.

As a result, the dialysate circulates from the dialysate supply channel 54 to the infusion channel 41, and then flows into the vein-side channel 21 of the blood circuit 3. With the blood pump 8 being in the attached state of the tube 33 as in the third step, the dialysate does not circulate past the blood pump 8, and thus flows from the artery-side channel 21, through the dialyzer 2, and into the vein-side channel 22.

Thereafter, after passing through the drip chamber 9, the dialysate circulates from the vein-side channel 22 to the third priming piping 72, and flows from the retransfusion channel 23 connected to the artery-side channel 21 into the artery-side channel 21.

At this moment as well, since the blood pump 8 is in the attached state of the tube 33, the dialysate circulates from the artery-side channel 21 into the fourth priming piping 73, and then flows into the priming channel 63 of the dialysate circuit 4.

The fourth step is thus completed. Thereafter, a healthcare worker removes the third priming piping 72 from the retransfusion channel 23A, and then connects the end portion of the retransfusion channel 23A to the first connection port P1 in the retransfusion channel 23B of the dialysate circuit 4, to thereby complete the priming operation.

Note that, in the third embodiment as well, the priming may be carried out in the state in which the retransfusion channel 23A and the retransfusion channel 23B are connected in order to bypass re-attachment of the retransfusion channel 23A after the completion of the fourth step, as described in the second embodiment.

In this case as well, a port to which the third priming piping 72 can be connected is provided in the artery-side channel 21, and the third priming piping 72 is connected to the port at the time of the priming operation.

Then, at the time of the priming operation, priming manipulation of the retransfusion channel 23A and the retransfusion channel 23B, which takes place in the third step of the first embodiment shown in FIG. 8, is carried out between the second step and the third step of the third embodiment.

Figure 19:
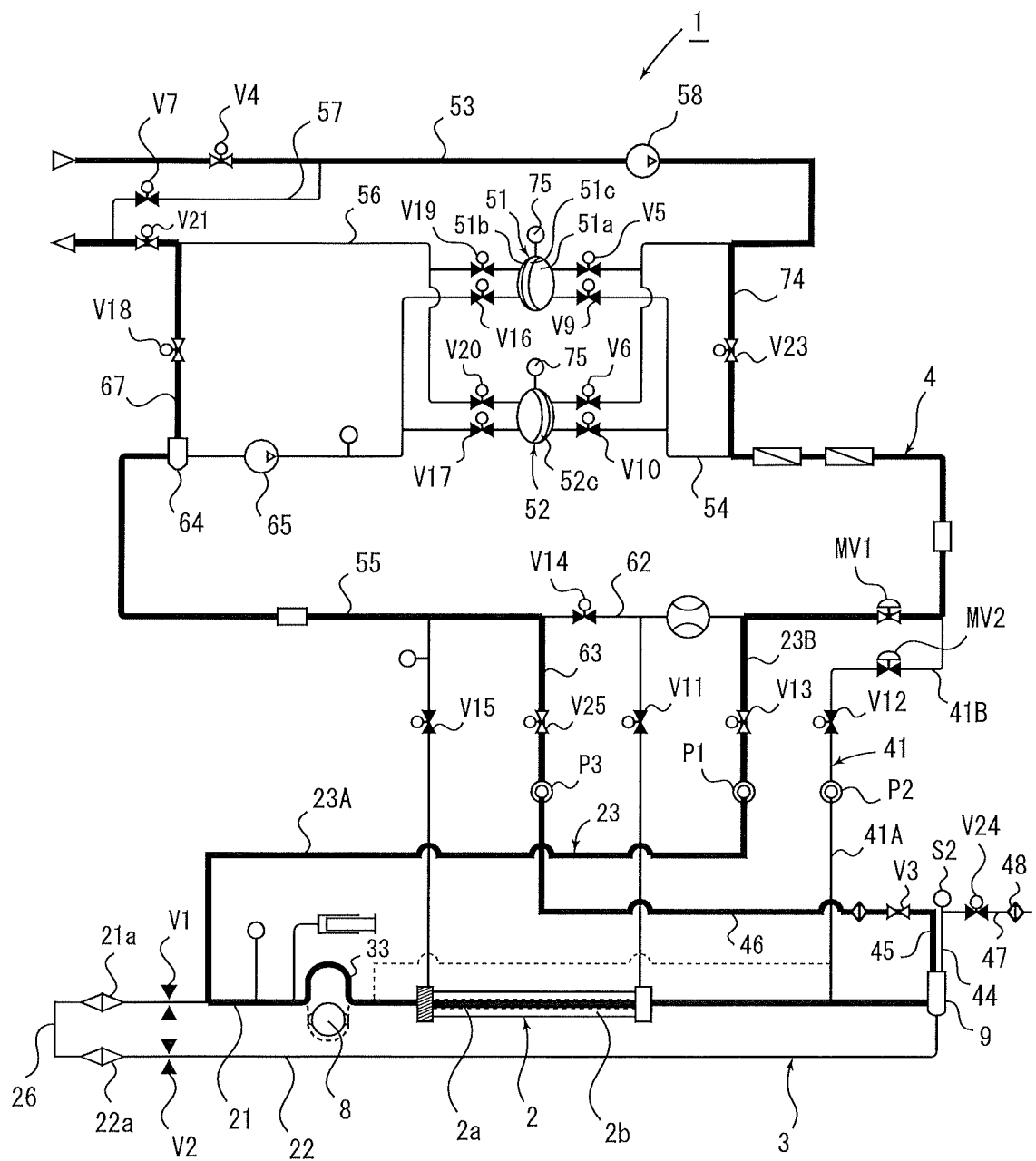
FIG. 19 is a circuit diagram illustrating a fourth embodiment.

Next, FIG. 19 illustrates the priming method for the dialysis apparatus 1 according to the fourth embodiment. The dialysis apparatus 1 shown in FIG. 19 is a so-called console-type dialysis apparatus 1, to which dialysate prepared in advance by a dialysate production device, not illustrated, is to be supplied.

In the dialysate circuit 4 in the dialysis apparatus 1 according to the present embodiment, a sixth bypass channel 74 is provided between the liquid replenishment channel 53 and the dialysate supply channel 54, the sixth bypass channel 74 being provided with a twenty-third valve V23 controlled by the control device.

In addition, in the present embodiment, the dialysate circuit 4 is not provided with the water removal channel 66 and the water removal pump 68. Instead, a triple-chamber type dialysis apparatus is employed in which variable capacity chambers 51c, 52c are formed between the supply chamber 51a and the collection chamber 51b in the first and second dialysate chambers 51 and 52.

The variable capacity chambers 51c, 52c are filled with silicone oil, and are each provided with an oil pump 75 that suctions and discharges the silicone oil with respect to the variable capacity chambers 51c, 52c. As the oil pump 75 suctions and discharges the silicone oil, the capacity of the variable capacity chambers 51c, 52c is changed.

Due to such a configuration, by discharging the silicone oil from the variable capacity chambers 51c, 52c to reduce the capacity during the dialysis treatment, negative pressure can be generated in the dialysate collection channel 55, whereby differential pressure is generated between the dialysate chamber 2b and the blood chamber 2a in the dialyzer 2 to carry out water removal.

On the other hand, the dialysate circuit 4 in the dialysis apparatus 1 according to the present embodiment is provided with the retransfusion channel 23B, the infusion channel 41B, and the priming channel 63 as in the first to third embodiments, with the first to third connection ports P1 to P3 being provided respectively in the end portions thereof.

With regard also to the dialyzer 2 and the blood circuit 3 to be attached to the dialysis apparatus 1, attachment thereof can be done in a similar manner to the first to third embodiments. Here, the blood circuit 3 is attached in a similar manner to the first embodiment, with the first priming piping 26 being connected between the artery-side channel 21 and the vein-side channel 22, and the second priming piping 46 being connected between the retransfusion channel 23A of the blood circuit 3 and the retransfusion channel 23B of the dialysate circuit 4.

With regard also to the blood pump 8 provided in the blood circuit 3, the one used in the first to third embodiments is used. The blood pump 8 is provided with a tube attachment device that permits attachment of the tube 33 to the housing 31 during the priming operation, in other words switching from the unattached state to the attached state.

Hereinafter, a priming operation for the dialysis apparatus 1 according to the fourth embodiment is described. FIG. 19 corresponds to the second step (FIG. 7) in the first embodiment.

Although not illustrated, in the first step in the fourth embodiment, the dialysate is circulated in the dialysate circuit 4, whereby the dialysate is circulated in the dialysate chamber 2b in the dialyzer 2, as in the first to third embodiments.

Subsequently, in the second step shown in FIG. 19, by opening the twenty-third valve V23 of the sixth bypass channel 74, the dialysate produced by the dialysate production device is circulated from the liquid replenishment channel 53 to the dialysate supply channel 54 by the liquid replenishment pump 58 as the liquid feeding pump provided in the liquid replenishment channel 53.

Subsequently, the dialysate flows from the dialysate supply channel 54 to the retransfusion channel 23 as in the first embodiment. In the vein-side channel 21 of the blood circuit 3, the tube 33 of the blood pump 8 is in the unattached state and the artery-side clamp V1 is closed, whereby the dialysate circulates past the blood pump 8 toward the dialyzer 2.

Furthermore, the dialysate having passed through the blood chamber 2a in the dialyzer 2 flows from the drip chamber 9, through the overflow channel 45 and the second priming piping 46, into the priming piping 63 of the dialysate circuit 4.

Thereafter, by carrying out operations similar to the third and fourth steps in the first embodiment except for feeding the dialysate by the liquid replenishment pump 58, the priming of the blood circuit 3 can be carried out in a similar manner to the first embodiment.

Thus, in the console-type dialysis apparatus 1 of the present embodiment, more specifically in the dialysis apparatus 1 in which the sixth bypass channel 74 is provided between the liquid replenishment channel 53 and the dialysate supply channel 54 in the dialysate circuit 4, the priming can be carried out through feeding the dialysate by the liquid replenishment pump 58 provided in the liquid replenishment channel 53.

As described above, since the liquid replenishment pump 58 is also configured with a magnetic gear pump, at the time of the priming, the dialysate can be rapidly circulated to the blood circuit 3 by feeding the dialysate by the liquid replenishment pump 58.

Therefore, in a similar manner to the first embodiment, feeding through the water hammer phenomenon can be carried out by opening and closing the thirteenth valve V13 of the retransfusion channel 23 at predetermined time intervals, thus enabling rapid priming.

Furthermore, also in the fourth embodiment, the dialysate flow in the blood circuit 3 can be controlled by switching the tube 33 from the unattached state to the attached state in the blood pump 8 and compressing to close the tube 33, as in the first to third embodiments.

Note that, also in the first to third embodiments, the priming can be carried out in a similar manner to the fourth embodiment if there are configurations corresponding to the sixth bypass channel 74 and the twenty-third valve V23 of the fourth embodiment.

In addition, although the first and second dialysate chambers 51, 52 of the dialysate circuit 4 in the first to third embodiments are configured in a double-chamber structure with the supply chamber 51a and the collection chamber 51b, it is also possible to omit the infusion channel and the infusion pump by employing chambers of a triple-chamber structure as in the fourth embodiment.

REFERENCE SIGNS LIST

1 Dialysis apparatus
2 Dialyzer
3 Blood circuit
4 Dialysate circuit
8 Blood pump
21 Artery-side channel
22 Vein-side channel
23 Retransfusion channel (connection channel)
26 First priming piping
31 Housing
32 Rotor
33 Tube
41 Infusion channel (connection channel)
46 Second priming piping
54 Dialysate supply channel
55 Dialysate collection channel
58 Liquid replenishment pump (liquid feeding pump)
65 Dialysate pump
P1 to P3 First to third connection ports

What is claimed is:

1. A dialysis apparatus comprising:
a dialyzer in which a blood chamber and a dialysate chamber are formed; a blood circuit that circulates blood to the blood chamber in the dialyzer; a dialysate circuit that circulates dialysate to the dialysate chamber in the dialyzer; a liquid feeding pump that is provided in the dialysate circuit and feeds the dialysate; a connection channel that communicatively connects the dialysate circuit and the blood circuit; and
a blood pump provided with a housing that houses an elastic tube comprised in the blood circuit and a rotor that rotates inside the housing to rotate the tube while compressing the tube,
the dialysate being circulated from the dialysate circuit to the blood circuit via the connection channel during a priming operation,
wherein:
the blood pump comprises a tube attachment device that switches from an unattached state in which the tube is positioned outside the housing and permits a liquid to circulate thereinside, to an attached state in which the tube is housed in the housing and the rotor compresses the tube to block the tube; and during the priming operation, with the blood pump being in the unattached state, the liquid feeding pump feeds the dialysate from the dialysate circuit to the blood circuit via the connection channel and, when a predetermined amount of the dialysate has circulated past the blood pump, the tube attachment device puts the blood pump into the attached state.

2. The dialysis apparatus according to claim 1, further comprising a valve provided in the connection channel and a control device that controls opening and closing of the valve, wherein, during the priming operation, in a state in which the liquid feeding pump in the dialysate circuit feeds the dialysate, the control device repeatedly opens and closes the valve in the connection channel to cause a water hammer phenomenon in the blood circuit communicatively connected to the connection channel and in the dialyzer.

3. The dialysis apparatus according to claim 1, wherein the liquid feeding pump provided in the dialysate circuit is a magnetic gear pump.

4. The dialysis apparatus according to claim 1, wherein the connection channel is either an infusion channel for use in infusion of the dialysate from the dialysate circuit to the blood circuit during dialysis treatment, or an infusion channel for use in retransfusion of the blood in the blood circuit to a patient by circulating the dialysate from the dialysate circuit to the blood circuit after the dialysis treatment.

5. A priming method for a dialysis apparatus, the dialysis apparatus comprising:

a dialyzer in which a blood chamber and a dialysate chamber are formed; a blood circuit that circulates blood to the blood chamber in the dialyzer; a dialysate circuit that circulates dialysate to the dialysate chamber in the dialyzer; a liquid feeding pump that is provided in the dialysate circuit and feeds the dialysate; a connection channel that communicatively connects the dialysate circuit and the blood circuit; and a blood pump provided with a housing that houses an elastic tube comprised in the blood circuit and a rotor that rotates inside the housing to rotate the tube while compressing the tube, the dialysate being circulated from the dialysate circuit to the blood circuit via the connection channel during a priming operation, wherein, during the priming operation, the tube is detached from the housing to be in an unattached state in which a liquid is permitted to circulate thereinside, and then the liquid feeding pump feeds the dialysate from the dialysate circuit to the blood circuit via the connection channel to circulate the dialysate to a portion past the blood pump.

6. The priming method for a dialysis apparatus according to claim 5, wherein, with the blood pump being in the unattached state, the liquid feeding pump feeds the dialysate from the dialysate circuit to the blood circuit via the connection channel to circulate a predetermined amount of the dialysate to the portion past the blood pump, and then the tube of the blood pump is attached to the housing and the rotor is stopped to obtain an attached state in which the tube is compressed by the rotor, whereby the dialysate is circulated in a direction opposite to the blood pump.

7. The priming method for a dialysis apparatus according to claim 5, wherein: a valve is provided in the connection channel; and during the priming operation, in a state in which the liquid feeding pump in the dialysate circuit feeds the dialysate, the valve in the connection channel is closed to increase an internal pressure of the connection channel and then the valve is opened, to cause a water hammer phenomenon in the blood circuit communicatively connected to the connection channel and in the dialyzer.

* * * * *